(12) United States Patent
Brannan et al.

(10) Patent No.: US 9,127,989 B2
(45) Date of Patent: Sep. 8, 2015

(54) MICROWAVE THERMOMETRY FOR MICROWAVE ABLATION SYSTEMS

(71) Applicant: Covidien LP, Mansfield, MA (US)

(72) Inventors: Joseph D. Brannan, Erie, CO (US); Casey M. Ladtkow, Erie, CO (US)

(73) Assignee: Covidien LP, Mansfield, MA (US)

( * ) Notice: Subject to any disclaimer, the term of this patent is extended or adjusted under 35 U.S.C. 154(b) by 195 days.

(21) Appl. No.: 13/924,277

(22) Filed: Jun. 21, 2013

(65) Prior Publication Data

US 2013/0345691 A1     Dec. 26, 2013

Related U.S. Application Data

(60) Provisional application No. 61/663,099, filed on Jun. 22, 2012, provisional application No. 61/809,634, filed on Apr. 8, 2013, provisional application No. 61/837,633, filed on Jun. 20, 2013.

(51) Int. Cl.
*A61B 18/18* (2006.01)
*G01K 11/00* (2006.01)
(Continued)

(52) U.S. Cl.
CPC .......... *G01K 11/006* (2013.01); *A61B 18/1815* (2013.01); *G01J 5/46* (2013.01);
(Continued)

(58) Field of Classification Search
CPC .............. A61B 2018/1823; A61B 2018/00791
USPC ............................ 606/33, 34, 38, 42; 374/122
See application file for complete search history.

(56) References Cited

U.S. PATENT DOCUMENTS

| D223,367 S | 4/1972 | Kountz |
|---|---|---|
| D263,020 S | 2/1982 | Rau, III |

(Continued)

FOREIGN PATENT DOCUMENTS

| CN | 1103807 A | 6/1995 |
|---|---|---|
| DE | 390937 C | 3/1924 |

(Continued)

OTHER PUBLICATIONS

LigaSureTM Vessel Sealing System, the Seal of Confidence in General, Gynecologic, Urologic, and Laparoscopic Surgery, Sales/Product Literature, Jan. 2004.

(Continued)

*Primary Examiner* — Joseph Stoklosa
*Assistant Examiner* — Jocelyn D Ram

(57) ABSTRACT

A microwave ablation system incorporates a microwave thermometer that couples to a microwave transmission network connecting a microwave generator to a microwave applicator to measure noise temperature. The noise temperature is processed to separate out components the noise temperature including the noise temperature of the tissue being treated and the noise temperature of the microwave transmission network. The noise temperature may be measured by a radiometer while the microwave generator is generating the microwave signal or during a period when the microwave signal is turned off. The microwave ablation system may be configured as a modular system having one or more thermometry network modules that are connectable between a microwave applicator and a microwave generator. Alternatively, the modular system includes a microwave generator, a microwave applicator, and a microwave cable that incorporate a microwave thermometry network module.

20 Claims, 19 Drawing Sheets

(51) Int. Cl.
*H01R 13/66* (2006.01)
*G01J 5/46* (2006.01)
*A61B 18/00* (2006.01)

(52) U.S. Cl.
CPC ...... *H01R 13/66* (2013.01); *A61B 2018/00577* (2013.01); *A61B 2018/00642* (2013.01); *A61B 2018/00791* (2013.01); *A61B 2018/00821* (2013.01)

(56) References Cited

U.S. PATENT DOCUMENTS

| | | | |
|---|---|---|---|
| 4,346,716 A * | 8/1982 | Carr | 600/407 |
| D266,842 S | 11/1982 | Villers et al. | |
| D278,306 S | 4/1985 | McIntosh | |
| 4,557,272 A * | 12/1985 | Carr | 600/549 |
| 4,583,589 A | 4/1986 | Kasevich | |
| D295,893 S | 5/1988 | Sharkany et al. | |
| D295,894 S | 5/1988 | Sharkany et al. | |
| 5,301,687 A | 4/1994 | Wong et al. | |
| 5,370,644 A | 12/1994 | Langberg | |
| D354,218 S | 1/1995 | Van de Peer | |
| 5,545,137 A | 8/1996 | Rudie et al. | |
| 5,603,697 A | 2/1997 | Grundy et al. | |
| 5,624,392 A | 4/1997 | Saab | |
| 5,688,050 A * | 11/1997 | Sterzer et al. | 374/122 |
| 5,693,082 A | 12/1997 | Warner et al. | |
| 5,741,071 A * | 4/1998 | Weiss et al. | 374/175 |
| 5,741,249 A | 4/1998 | Moss et al. | |
| 5,974,343 A * | 10/1999 | Brevard et al. | 607/102 |
| 5,993,447 A | 11/1999 | Blewett et al. | |
| 5,995,875 A | 11/1999 | Blewett et al. | |
| 6,014,581 A | 1/2000 | Whayne et al. | |
| D424,693 S | 5/2000 | Pruter | |
| D424,694 S | 5/2000 | Tetzlaff et al. | |
| D425,201 S | 5/2000 | Tetzlaff et al. | |
| 6,061,551 A | 5/2000 | Sorrells et al. | |
| 6,106,524 A | 8/2000 | Eggers et al. | |
| 6,117,101 A | 9/2000 | Diederich et al. | |
| 6,139,527 A | 10/2000 | Laufer et al. | |
| 6,210,367 B1 | 4/2001 | Carr | |
| 6,277,113 B1 | 8/2001 | Berube | |
| D449,886 S | 10/2001 | Tetzlaff et al. | |
| D457,958 S | 5/2002 | Dycus et al. | |
| D457,959 S | 5/2002 | Tetzlaff et al. | |
| 6,398,781 B1 | 6/2002 | Goble et al. | |
| 6,485,486 B1 | 11/2002 | Trembly et al. | |
| 6,496,737 B2 | 12/2002 | Rudie et al. | |
| 6,496,738 B2 | 12/2002 | Carr | |
| 6,514,249 B1 | 2/2003 | Maguire et al. | |
| 6,547,788 B1 | 4/2003 | Maguire et al. | |
| 6,599,288 B2 | 7/2003 | Maguire et al. | |
| 6,629,974 B2 | 10/2003 | Penny et al. | |
| 6,635,055 B1 | 10/2003 | Cronin | |
| 6,652,515 B1 | 11/2003 | Maguire et al. | |
| 6,676,657 B2 | 1/2004 | Wood | |
| D487,039 S | 2/2004 | Webster et al. | |
| 6,706,040 B2 | 3/2004 | Mahon et al. | |
| 6,723,091 B2 | 4/2004 | Goble et al. | |
| 6,740,108 B1 | 5/2004 | Just et al. | |
| 6,770,070 B1 | 8/2004 | Balbierz | |
| D496,997 S | 10/2004 | Dycus et al. | |
| D499,181 S | 11/2004 | Dycus et al. | |
| 6,869,431 B2 | 3/2005 | Maguire et al. | |
| 6,893,436 B2 | 5/2005 | Woodard et al. | |
| 6,932,776 B2 | 8/2005 | Carr | |
| 6,997,925 B2 | 2/2006 | Maguire et al. | |
| 7,004,938 B2 | 2/2006 | Ormsby et al. | |
| D525,361 S | 7/2006 | Hushka | |
| 7,089,063 B2 | 8/2006 | Lesh et al. | |
| D531,311 S | 10/2006 | Guerra et al. | |
| D533,942 S | 12/2006 | Kerr et al. | |
| D535,027 S | 1/2007 | James et al. | |
| 7,197,356 B2 | 3/2007 | Carr | |
| D541,418 S | 4/2007 | Schechter et al. | |
| 7,200,445 B1 | 4/2007 | Dalbec et al. | |
| D541,938 S | 5/2007 | Kerr et al | |
| 7,261,001 B2 | 8/2007 | Heijnsdijk et al. | |
| 7,263,398 B2 | 8/2007 | Carr | |
| 7,294,125 B2 | 11/2007 | Phalen et al. | |
| 7,300,436 B2 | 11/2007 | Penny et al. | |
| 7,303,558 B2 | 12/2007 | Swanson | |
| D564,662 S | 3/2008 | Moses et al. | |
| 7,402,168 B2 | 7/2008 | Sanderson et al. | |
| 7,410,486 B2 | 8/2008 | Fuimaono et al. | |
| D576,932 S | 9/2008 | Strehler | |
| D594,736 S | 6/2009 | Esjunin | |
| D594,737 S | 6/2009 | Kelly et al. | |
| 7,611,508 B2 | 11/2009 | Yang et al. | |
| D606,203 S | 12/2009 | Husheer et al. | |
| D613,412 S | 4/2010 | DeCarlo | |
| 7,734,330 B2 | 6/2010 | Carr | |
| 7,769,469 B2 | 8/2010 | Carr et al. | |
| D634,010 S | 3/2011 | DeCarlo | |
| 7,921,855 B2 | 4/2011 | Danek et al. | |
| 7,933,660 B2 | 4/2011 | Carr | |
| 8,292,881 B2 | 10/2012 | Brannan et al. | |
| D681,810 S | 5/2013 | DeCarlo | |
| 2002/0022836 A1 | 2/2002 | Goble et al. | |
| 2004/0097805 A1 | 5/2004 | Verard et al. | |
| 2004/0133254 A1 | 7/2004 | Sterzer et al. | |
| 2005/0215942 A1 | 9/2005 | Abrahamson et al. | |
| 2006/0009833 A1 | 1/2006 | Chobotov et al. | |
| 2006/0089637 A1 | 4/2006 | Werneth et al. | |
| 2006/0167416 A1 | 7/2006 | Mathis et al. | |
| 2007/0027385 A1 | 2/2007 | Brister et al. | |
| 2007/0129717 A1 | 6/2007 | Brown et al. | |
| 2007/0185554 A1 | 8/2007 | Appling et al. | |
| 2007/0282319 A1 | 12/2007 | van der Weide et al. | |
| 2008/0147056 A1 | 6/2008 | van der Weide et al. | |
| 2008/0208031 A1 | 8/2008 | Kurpad et al. | |
| 2008/0208039 A1 | 8/2008 | Kurpad et al. | |
| 2009/0076409 A1 | 3/2009 | Wu et al. | |
| 2009/0187180 A1 | 7/2009 | Brannan | |
| 2009/0222002 A1 | 9/2009 | Bonn et al. | |
| 2009/0312754 A1 | 12/2009 | Lenihan et al. | |
| 2010/0036369 A1 | 2/2010 | Hancock | |
| 2010/0076424 A1 | 3/2010 | Carr | |
| 2010/0185191 A1 * | 7/2010 | Carr et al. | 606/33 |
| 2010/0262134 A1 | 10/2010 | Jensen et al. | |
| 2011/0004205 A1 | 1/2011 | Chu et al. | |
| 2011/0034913 A1 | 2/2011 | Brannan | |
| 2011/0034917 A1 | 2/2011 | Brannan | |
| 2011/0040300 A1 | 2/2011 | Brannan | |
| 2011/0054458 A1 | 3/2011 | Behnke | |
| 2011/0077634 A1 | 3/2011 | Brannan | |
| 2011/0118721 A1 | 5/2011 | Brannan | |
| 2011/0130750 A1 | 6/2011 | Ormsby et al. | |
| 2011/0166518 A1 | 7/2011 | Nguyen et al. | |
| 2011/0166519 A1 | 7/2011 | Nguyen et al. | |
| 2011/0282336 A1 | 11/2011 | Brannan et al. | |
| 2011/0301587 A1 | 12/2011 | Deem et al. | |
| 2011/0306969 A1 * | 12/2011 | Coe et al. | 606/41 |
| 2012/0029359 A1 * | 2/2012 | Sterzer et al. | 600/474 |
| 2012/0035603 A1 | 2/2012 | Lenihan | |
| 2012/0065481 A1 | 3/2012 | Hunter et al. | |
| 2013/0204240 A1 * | 8/2013 | McCarthy et al. | 606/21 |
| 2013/0345693 A1 * | 12/2013 | Brannan | 606/33 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 250428 A1 | 8/1976 |
| DE | 2627679 A1 | 1/1977 |

(56) References Cited

FOREIGN PATENT DOCUMENTS

| | | |
|---|---|---|
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1034747 A1 | 9/2000 |
| EP | 1034748 | 9/2000 |
| EP | 1055400 | 11/2000 |
| EP | 1 159 926 A2 | 12/2001 |
| EP | 2147651 A1 | 1/2010 |
| EP | 2322113 A1 | 5/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| JP | 05-293088 B2 | 9/2013 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 94/16632 A1 | 8/1994 |
| WO | 97/24074 A1 | 7/1997 |
| WO | 00/36985 A2 | 6/2000 |
| WO | 0057811 A1 | 10/2000 |
| WO | 0100114 A1 | 1/2001 |
| WO | 02/45790 A2 | 6/2002 |
| WO | 2008/068485 A2 | 6/2008 |
| WO | 2010/035831 A1 | 4/2010 |

OTHER PUBLICATIONS

Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Dec. 1999) "FlexStrand": product description, 1 page.
Mdtech product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/1977).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

(56) References Cited

OTHER PUBLICATIONS

Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1996, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.

(56) References Cited

OTHER PUBLICATIONS

Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, Vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brennan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
International Search Report from corresponding PCT/US2013/047122 dated Sep. 5, 2013.
International Search Report from corresponding PCT/US2013/047130 dated Sep. 5, 2013.
International Search Report from corresponding PCT/US2013/047116 dated Oct. 10, 2013.

* cited by examiner

FIG. 3A  FIG. 3B

MICROWAVE THERMOMETRY FOR MICROWAVE ABLATION SYSTEMS

CROSS-REFERENCE TO RELATED APPLICATIONS

This application claims the benefit of, and priority to, U.S. Provisional Patent Application No. 61/663,099 filed on Jun. 22, 2012, U.S. Provisional Patent Application No. 61/809,634 filed on Apr. 8, 2013, and U.S. Provisional Patent Application No. 61/837,633 filed on Jun. 20, 2013, the entire contents of each of which are incorporated by reference herein for all purposes.

BACKGROUND

1. Technical Field

The present disclosure relates to microwave thermometry in microwave ablation systems.

2. Discussion of Related Art

Electromagnetic radiation can be used to heat and destroy tumor cells. Treatment may involve inserting ablation probes into tissues where cancerous tumors have been identified. Once the ablation probes are properly positioned, the ablation probes emit electromagnetic radiation into tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat or ablate tissue.

Electrosurgical devices utilizing electromagnetic radiation have been developed for a variety of uses and applications. Typically, apparatus for use in ablation procedures include a power generation source, e.g., a microwave or radio frequency (RF) electrosurgical generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback and identification signals between the instrument and the generator.

There are several types of microwave probes in use, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

Because of the small temperature difference between the temperature required for denaturing malignant cells and the temperature normally injurious to healthy cells, precise temperature measurements are needed to lead to more predictable temperature distribution to eradicate the tumor cells while minimizing the damage to healthy tissue surrounding the tissue to which microwave energy is being applied. Implantable thermoprobes, such as thermocouples or optical fibers, are typically used to measure tissue temperature. These measurements, however, are limited to a small volume of tissue surrounding the measuring point of the thermoprobes.

SUMMARY

In one aspect, the present disclosure features a microwave ablation system including a microwave applicator, a microwave generator coupled to the microwave applicator, a thermometry circuit coupled between the microwave generator and the microwave applicator, and a controller coupled to the thermometry circuit. The microwave applicator includes an antenna that delivers microwave energy to ablate tissue and the microwave generator generates a microwave signal and transmits the microwave signal to the antenna via a transmission network. The thermometry circuit includes a radiometer that measures a noise temperature signal and a coupling network, which is coupled to the transmission network, that provides a noise temperature signal propagating in the transmission network to the radiometer. The controller calculates a temperature value based on the noise temperature signal.

The transmission network may include a microwave cable connected between the microwave applicator and the microwave generator and the thermometry circuit may be integrated into the microwave applicator, the microwave generator, or the microwave cable.

The thermometry circuit may include a first filter that isolates the noise temperature signal from the microwave signal generated by the microwave generator. The thermometry circuit may include a second filter that filters the output from the first filter to obtain a noise temperature signal from the tissue and a noise temperature signal from a component of the microwave ablation system. The component of the microwave ablation system may be a microwave cable connected between the microwave applicator and the microwave generator.

The coupling network may couple a portion of the signals propagating through the transmission network to the radiometer. The coupling network may be a directional coaxial coupler. The coupling network may alternatively be a switch that switches from a connection between the antenna and the microwave generator to a connection between the antenna and the radiometer. In yet another alternative, the coupling network may be a T-network having a first band pass filter for passing the noise temperature signal to the radiometer and a second band pass filter for passing the microwave signal to the antenna.

The radiometer may include a low-noise amplifier that amplifies the temperature noise signal, a detector coupled to the output of the intermediate frequency amplifier to detect the noise temperature signal, and an integrator coupled to the output of the detector. The radiometer may also include a local oscillator, a mixer coupled to the output of the low-noise amplifier and the output of the local oscillator to mix the amplified noise temperature signal with the output from the local oscillator, an intermediate frequency band pass filter coupled to the output of the mixer and having a predetermined bandwidth, and an intermediate frequency amplifier coupled to the output of the intermediate frequency band pass filter. Alternatively, the radiometer may also include a resistive load maintained at a constant temperature and a switch coupled to the input of the low-noise amplifier to switch the input of the low-noise amplifier between the antenna and the resistive load. The resistive load may be a thermocouple disposed in thermal communication with the transmission network. The integrator may integrate over a long period from 10 ms to 10 seconds and the predetermined bandwidth may be within ±35 MHz.

The controller of the microwave ablation system may calibrate the radiometer to the temperature of a body whose tissue is being treated by the microwave applicator. The controller may also control the microwave generator based on the temperature value.

In another aspect, the present disclosure features a microwave ablation device including an antenna that delivers microwave energy to ablate tissue and a handle assembly attached to the antenna. The handle assembly includes a thermometry circuit coupled to the antenna via a transmission network. The thermometry circuit includes a radiometer that measures a noise temperature signal, a coupling network coupled to the transmission network to provide a noise temperature signal propagating in the transmission network to the radiometer, and a controller, which is coupled to the thermometry circuit, that calculates a temperature value based on the noise temperature signal.

The thermometry circuit may include a first filter that isolates the noise temperature signal from a microwave signal propagating in the transmission network. The thermometry circuit may also include a second filter that filters the output from the first filter to obtain a noise temperature signal of the tissue and a noise temperature signal of the transmission network.

BRIEF DESCRIPTION OF THE DRAWINGS

Objects and features of the presently disclosed energy-delivery devices with a fluid-cooled probe assembly and systems including the same will become apparent to those of ordinary skill in the art when descriptions of various embodiments thereof are read with reference to the accompanying drawings, of which:

FIGS. 3A-3C are block diagrams showing embodiments of the coupling circuit of FIGS. 1 and 2;

DETAILED DESCRIPTION

Figure 1:
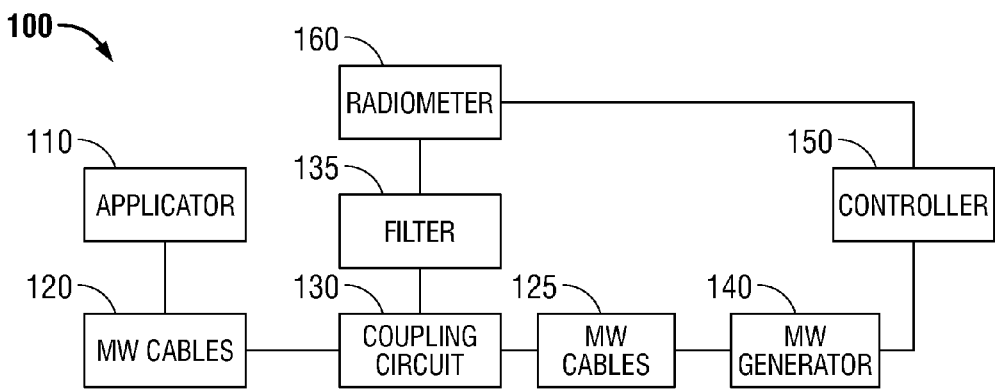
FIG. 1 is a block diagram of a microwave ablation system in accordance with embodiments of the present disclosure.

The present disclosure is generally directed to microwave ablation systems that incorporate a microwave thermometry network for monitoring the thermal characteristics of the microwave transmission network and the physiological environment surrounding a microwave applicator. Microwave radiometry is a technique for measuring electromagnetic energy considered as thermal radiation, and can be used to detect and measure microwave energy emanating from heat sources.

The microwave ablation systems according to the present disclosure combine an antenna transmitting energy to ablate tissue (at a set "ablation frequency") with an antenna receiving thermal noise power emitted by heated tissue (at a set "radiometric frequency") that can be translated into average temperature. If the radiometric frequency is high enough (e.g., 3-9 GHz), the temperature will be averaged over a small enough volume around the antenna (e.g., 1-3 mm), allowing the antenna to be used as a thermocouple.

The microwave ablation systems according to the present disclosure use microwave thermometry in combination with the pre-existing transmission network of a microwave ablation system to enable thermal monitoring of tissue and microwave ablation system components without increasing the size of a microwave applicator's catheter or its shaft cross section. These systems provide real-time monitoring and feedback of tissue temperature, which enhances procedural outcomes through real-time verification of ablation progression, completeness, or lack of completeness. The monitoring of system component temperature allows for the microwave ablation system to insure adequate cooling is occurring throughout a procedure thereby preventing potential device failures or potential patient or user injury.

Embodiments of the microwave ablation systems and components are described with reference to the accompanying drawings. Like reference numerals may refer to similar or identical elements throughout the description of the figures. As shown in the drawings and as used in this description, the term "proximal" refers to that portion of the apparatus, or component of the apparatus, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection.

As it is used in this description, "energy applicator" generally refers to any device that can be used to transfer energy from a power generating source, such as a microwave or RF electrosurgical generator, to tissue. For the purposes of the present disclosure, the term "energy applicator" is interchangeable with the term "energy-delivery device". As it is used in this description, "transmission line" generally refers to any transmission medium that can be used for the propagation of signals from one point to another. As it is used in this description, "fluid" generally refers to a liquid, a gas or both.

As it is used in this description, the term "controller" refers to any electrical device that employs digital and/or analog components to generate digital and/or analog signals to control or drive another device. The term "controller" may refer to a digital signal processor, a microcontroller, or a computer having a processor, a memory, and input/output ports for carrying out some of the methods described herein.

FIG. 1 is a block diagram of a microwave ablation system 100 according to embodiments of the present disclosure. The microwave ablation system 100 includes a microwave applicator 110, microwave cables 120 and 125, a coupling circuit 130, a microwave generator 140, a filter 135, and a radiometer 160. The microwave generator 140 generates a microwave signal and outputs it to the microwave applicator 110 via the microwave cables 120 and 125. The microwave applicator 110 includes at least one antenna which emits microwave radiation when the microwave signal is applied to the antenna. The antenna may be disposed in a tumor so that the microwave radiation emitted from the antenna can ablate the tumor.

The coupling circuit 130 is coupled between the microwave generator 140 and the microwave applicator 110 to provide a noise temperature signal or at least a portion of the signals propagating through the microwave cables 120 and 125 to the radiometer 160. The filter 135 isolates a noise temperature signal from the at least a portion of the microwave signal. Then, the radiometer 160 samples the noise temperature signal and provides it to the controller 150. The controller 150 may convert the microwave noise temperature signal into a temperature reading by digitally sampling the microwave noise temperature signal using an analog-to-digital converter (ADC) and scaling the result. The controller 150 may also interface with a display to display the temperature reading as described in more detail below.

The noise temperature measured by the radiometer 160 may be used to enable temperature feedback control. The feedback control may involve open loop control, e.g., user-based control, or closed loop control, e.g., for an autonomous system, to achieve a desired tissue effect and to improve the overall procedural outcome. The radiometer 160 and controller 150 may also be used to monitor the temperature of components of the microwave ablation system 100. For example, the radiometer 160 and controller 150 may be used to monitor the temperature of the microwave cables 120 to insure adequate cooling and to avoid failures.

Figure 2:
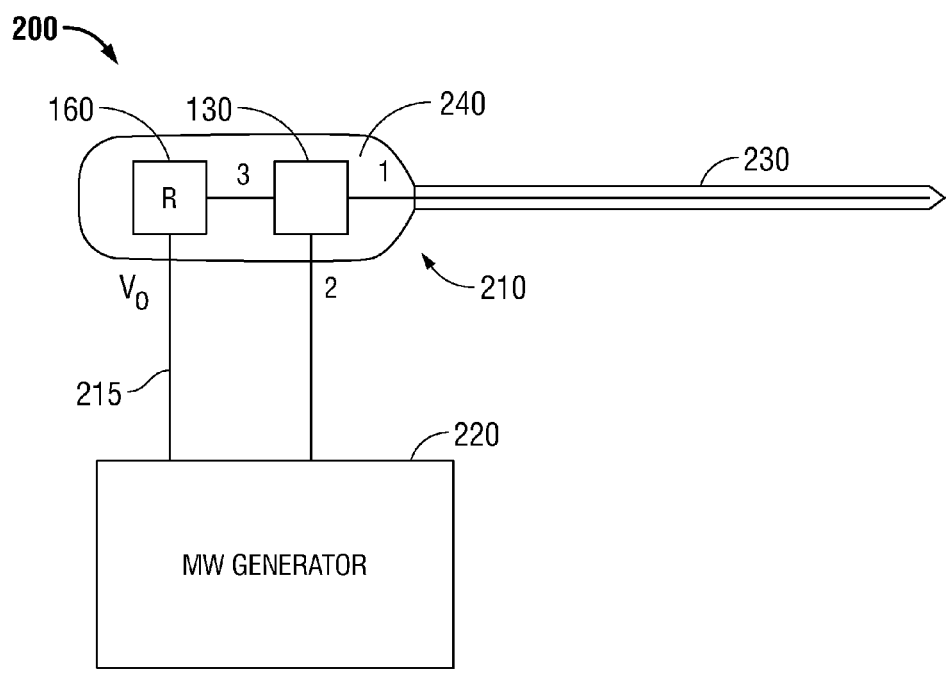
FIG. 2 is a block diagram of a microwave generator and a microwave applicator that incorporates the radiometer of the microwave ablation system of FIG. 1 in accordance with an embodiment of the present disclosure.

FIG. 2 is a block diagram of a microwave ablation system 200 according to some embodiments of the present disclosure. The microwave ablation system 200 includes a microwave generator 220 and a microwave applicator 210 coupled to the microwave generator 220. The microwave applicator 210 includes a microwave antenna 230 and a handle 240 coupled to the microwave antenna 230 to allow a clinician to manipulate the microwave antenna 230 during a microwave ablation procedure.

The microwave antenna 230 may be embodied as an inflexible ablation catheter or a flexible ablation catheter to accommodate a specific surgical procedure, a specific luminal structure, specific target tissue, a clinician's preference, etc. For example, in one embodiment, it may prove advantageous to have an ablation catheter that is very flexible for movement through the relatively narrow airways of the lungs of a patient. In some cases, it may prove advantageous to have an ablation catheter that is only slightly flexible, e.g., where the ablation catheter is needed to pierce or puncture tissue. Still further, to achieve the desired amount of flexibility, it may be desirable to employ the ablation catheter described in U.S. patent application Ser. No. 13/834,581 entitled "Microwave Energy-Delivery Device and System," the entire contents of which is incorporated herein by reference. It should be understood to those of skill in the art that the microwave antenna 230 may employ other ablation catheter embodiments, either simplified or more complex in structural detail, without departing from the scope of the instant disclosure.

To obtain accurate temperature measurements, the radiometer 160 is disposed as close as possible to the radiating portion of the microwave antenna 230 to limit unwanted noise from entering the radiometer 160. For example, as shown in FIG. 2, the radiometer 160 and the coupling circuit 130 are disposed within the handle 240 of the microwave applicator 210. The coupling circuit 130 is coupled between microwave feed transmission line and the antenna element to provide at least a portion of a microwave signal propagating in the antenna element to the radiometer 160. The radiometer 160 is coupled to the coupling circuit 130 and outputs a voltage signal $V_0$ that is proportional to the temperature of the environment surrounding the antenna 230, e.g., the tissue to be ablated. This voltage signal $V_0$ is provided to the microwave generator 220 via communication line 215.

Figure 3C:
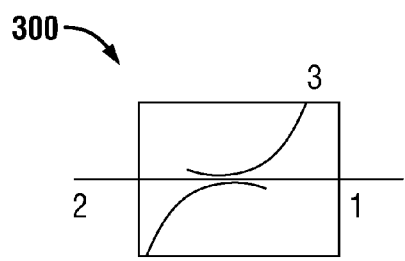
Figure 3C:
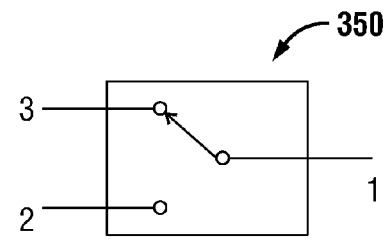
Figure 3C:
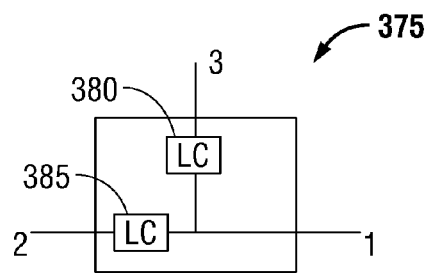

The coupling circuit 130 of FIGS. 1 and 2 may be any microwave coupling network which guides energy into the radiometer 160. FIGS. 3A-3C are block diagrams of exemplary embodiments of the coupling circuit 130 of FIGS. 1 and 2. FIG. 3A is a block diagram of a directional coupler 300 which couples a portion of the signals propagating in the microwave transmission line to port 3. The portion of the signals is then provided to the radiometer, which measures a noise temperature signal in the portion of the signals. FIG. 3B is a block diagram of a switch 350 that switches between ports 2 and 3. In some embodiments, the switch 350 is normally switched to port 2 so that the microwave signal is provided to the microwave antenna and is periodically switched to port 3 at regular intervals so that the radiometer can obtain noise temperature measurements. In other embodiments, the switch 350 may switch to port 3 at predetermined times during the microwave ablation procedure, e.g., near the beginning and near the end of a microwave ablation procedure. The switch 350 may include a solid-state switch, such as a diode switch, or a transfer-type switch, such as a mechanical relay.

As shown in FIG. 3C, the coupling circuit 130 may alternatively include a T-network 375 having a first LC resonant band pass filter 380 for passing one or more noise temperature frequencies to the radiometer 160 and a second LC resonant band pass filter 385 for passing the microwave signal to the microwave applicator.

Figure 4A:
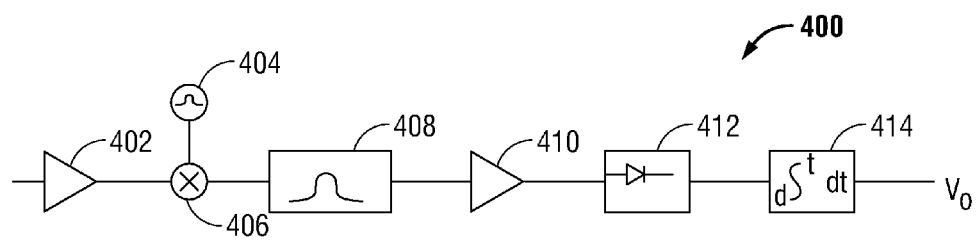
FIG. 4A is a circuit block diagram of the radiometer of FIGS. 1 and 2 in accordance with an embodiment of the present disclosure.

FIG. 4A is a circuit block diagram of a radiometer 400, which may be employed in the microwave ablation systems of FIGS. 1 and 2. The radiometer 400 includes a low-noise amplifier 402, a local oscillator 404, a frequency mixer 406, a band pass filter 408, an intermediate frequency (IF) amplifier 410, a detector 412, and an integrator 414. The low-noise amplifier 402 amplifies a noise temperature signal to obtain an amplified noise temperature signal. The local oscillator 404 produces a sine wave and the frequency mixer 406 mixes the amplified noise temperature signal with the sine wave to shift the noise temperature signal to an intermediate frequency (IF) that is lower than the frequency of the microwave signal. The intermediate frequency may be a frequency in the range from 100 Hz to 100 kHz, such as 10 kHz.

The band pass filter 408 filters the signal output from the frequency mixer 406 and the IF amplifier 410 amplifies the filtered signal. The detector 412 detects the noise temperature signal and the integrator 414 integrates the detected noise temperature signal to provide a voltage signal that is proportional to the temperature of the environment surrounding the microwave antenna. To overcome gain fluctuations and to improve the accuracy of temperature measurements, the radiometer 400 may use an integrator having long integration times, e.g., 10 ms to 10 s, and a band pass filter having a narrow bandwidth B, e.g., ±35 MHz centered around 3.5 GHz.

The voltage signal output from the radiometer 400 may be further processed to filter the signals propagating through the transmission network to obtain the noise temperature signal. For example, the radiometer 400 may use time domain and/or frequency domain filtering techniques to isolate the noise temperature signal, the noise temperature signal of the tissue, and the noise temperature signal of the transmission network.

Figure 4B:
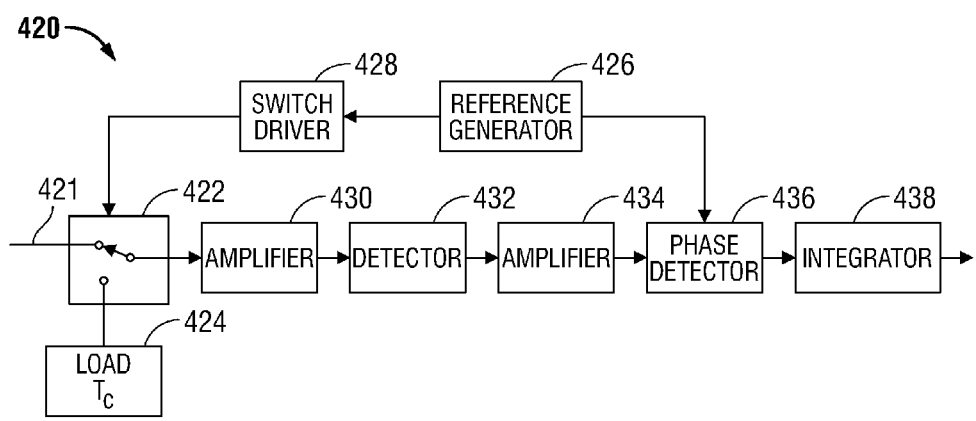
FIG. 4B is a circuit block diagram of the radiometer of FIGS. 1 and 2 in accordance with another embodiment of the present disclosure.

FIG. 4B is a circuit block diagram of a radiometer 420 in accordance with another embodiment of the present disclosure. The radiometer 400 includes a switch 422 (also referred to as a "Dicke modulator") that switches between the microwave signal input 421 and a resistive load 424, which is maintained at a constant temperature $T_C$. The resistive load 424 may be a thermocouple that is disposed in thermal communication with the transmission network so as to measure a temperature representative of the temperature of the transmission network. The resistive load 424 provides a reference temperature that is used to cancel out the noise temperature of the transmission network in order to isolate the noise temperature of the tissue. The switch may be a single pole, double throw switch. A reference generator 426 generates a control signal that is provided to the switch 422 via a switch driver 428 to control the switching frequency of the switch 422.

The output from the switch 422 is fed to an amplifier 430 which amplifies a noise temperature signal passing into the microwave signal input 421 or the reference temperature signal passing into the load temperature signal input 424. The amplifier 430 may be a low noise amplifier so that the amplifier does not introduce noise into the noise temperature signal. The output from the amplifier 430 is fed to an envelope detector 432 that detects the amplitude of the noise temperature signal. The amplitude of the noise temperature signal is amplified by amplifier 434 and provided to a phase detector 436. The reference generator 426 controls the phase detector 436 so that it operates synchronously with the switching of the switch 422. The output from the phase detector 436 is then integrated by the integrator 438, which reduces the amplitude of fluctuations in the noise temperature signal.

In operation, the reference generator 426 generates a square wave at a frequency higher (e.g., 30 to 1000 Hz) than the frequency at which receiver gain variations occur. The switch driver 428 drives the switch 422 in accordance with the generated square wave. By doing this, the effect of the receiver gain variations, e.g., amplifier drift, on the received noise temperature is eliminated.

Figure 5:
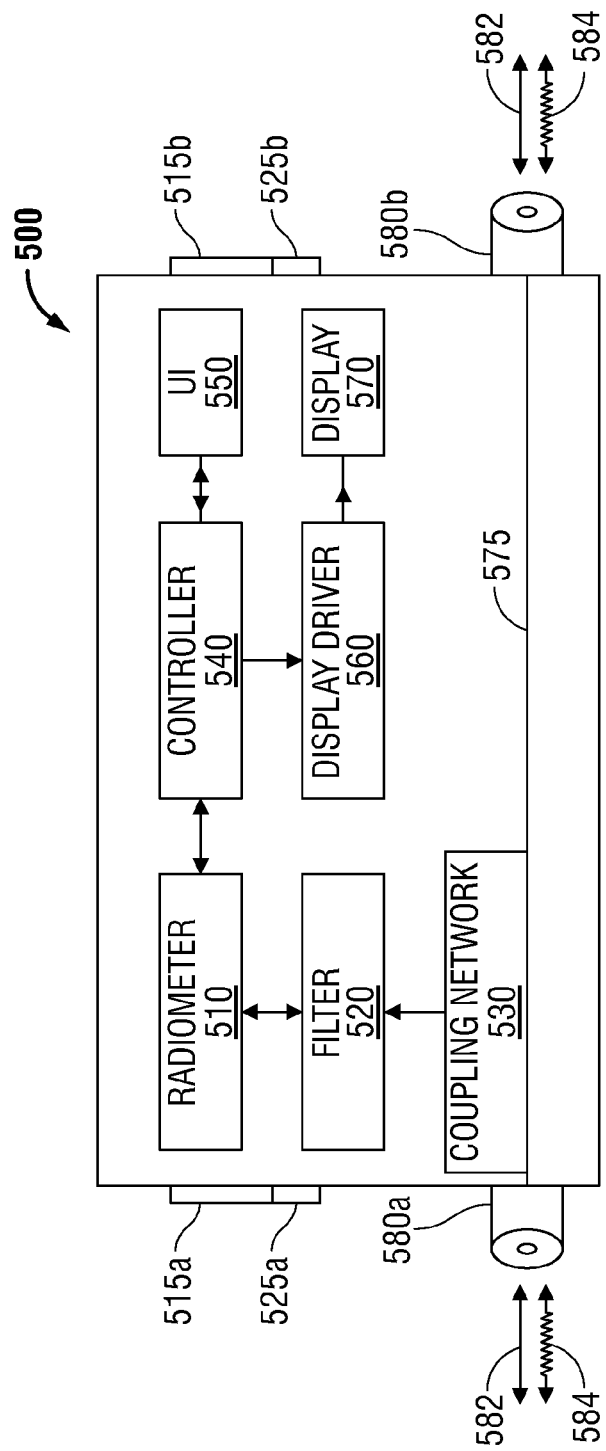
FIG. 5 is a block diagram of a microwave thermometry network used in the microwave ablation system of FIG. 1.

FIG. 5 is a block diagram of a microwave thermometry network module 500 used in the microwave ablation system of FIG. 1. The microwave thermometry network module 500 monitors the thermal characteristics of the microwave transmission network, e.g., the antenna, as well as the physiological environment, e.g., tissue, surrounding a microwave applicator. The microwave thermometry network module 500 includes a radiometer 510, a filter 520, transmission line connectors 580a and 580b, a transmission line 575 connected between the transmission line connectors 580a and 580b, and a coupling network 530 coupled to the transmission line 575.

The coupling network 530 couples at least a portion of the signals propagating through the transmission line 575 to the filter 520. These signals include a high power microwave signal 582 and a noise temperature signal 584. The filter 520 filters the signals provided by the coupling network 530 to isolate the noise temperature signal 584. For example, the filter 520 may isolate a high frequency noise temperature signal, e.g., a 4 GHz noise temperature signal, from a lower frequency high power microwave signal, e.g., a 2450 MHz microwave signal. The filter 520 may further filter the noise temperature signal to obtain the noise temperature signal from the tissue and the noise temperature signal from components of the microwave ablation system, such as the noise temperature signal from the microwave transmission network. Time and/or frequency domain signal processing techniques can be used to separate out the high power microwave signal, the microwave noise temperature from the tissue, and the microwave noise temperature from components of the microwave ablation system. For example, the filter 520 may employ a fast Fourier transform (FFT) to determine the amplitude of the noise temperature signal.

The filter 520 could be a variety of analog and digital electronic components intended to isolate the microwave signal from noise temperature signals. For example, the filter 520 may be implemented using digital circuitry, in which case the filter 520 would include an analog-to-digital converter (ADC) for converting at least a portion of the microwave signal provided by the coupling network 530 into digital form. The digital circuitry may implemented in a digital signal processor or a field-programmable gate array (FPGA). Noise temperature signals may be further separated into noise temperatures from each of the sources of noise temperature in the microwave ablation system (e.g., cables, circulators, couplers, filters, connectors, amplifiers, etc) and sources from the tissue. Also, the controller 540 can generate control signals, e.g., pulsing control signals, for controlling the microwave generator to adjust its output to improve or optimize the radiometer measurements as described, for example, in more detail below.

The microwave thermometry network module 500 further includes the controller 540, a user interface (UI) 550, a display driver 560, a display 570, and data bus connectors 515a and 515b. The controller 540 receives the measured noise temperature data from the radiometer 510 and determines temperature information based on the measured noise temperature data. Under the control of the controller 540, the temperature information may be directly displayed to the user of the system via the display driver 560 and the display 570 to inform the user of the real-time status, e.g., the progress or completion, of a medical procedure. The controller 540 may also use the temperature information as an input to a feedback algorithm designed to optimize the overall therapeutic effectiveness of the system as well as to insure system robustness and patient and user safety.

The real-time procedural monitoring performed by the microwave thermometry network module 500 may directly display a temperature value via the display 570 to the user which corresponds to the status of the ablation procedure, e.g., ablation completeness or incompleteness. The system robustness monitoring performed by the controller 540 may monitor the temperature of the microwave transmission network, i.e., the coaxial transmission lines and antenna, and limit microwave output power based on predetermined temperature limits placed on the microwave transmission network.

The user interface (UI) 550 may provide various levels of interface between the thermometry network module 500 and other components of the microwave ablation system ranging from minimally interfaced to highly interfaced. The minimally interfaced thermometry network module 500 may display a temperature value to the user, in which case the interface to the thermometry network module would include power supply line connectors 525a and 525b for distributing power to the components of the thermometry network module 500 and other components of the microwave ablation system connected to the power supply line connectors 525a and 525b. The minimally interfaced thermometry network module 500 would also include the coupling network 530 for coupling to the transmission line 575.

The highly interfaced thermometry network module would be a thermometry network module further including the controller 540 acting as the master controller of the microwave ablation system, in which case the interface to the thermometry network module 500 includes data bus connectors 515a and 515b through which mixed signal control and monitoring data is transmitted from the controller 540 to other components of the microwave ablation system connected to the thermometry network module 500 via the data bus connectors 515a and 515b. For example, the controller 540 may send commands to the microwave generator via connector 515b to vary characteristics of the microwave signal or stop the generation of the microwave signal entirely.

Figure 6:
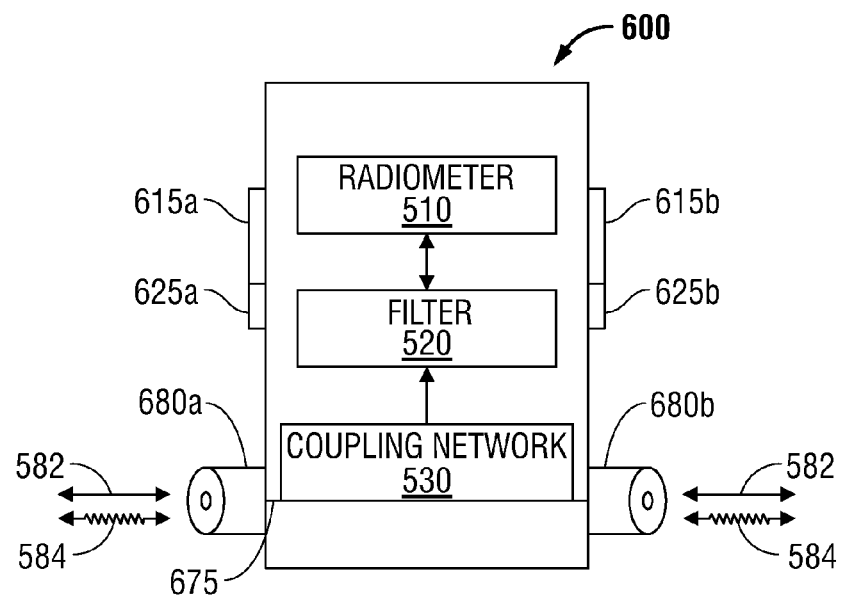
FIG. 6 is a block diagram of a radiometer module according to a split configuration of the microwave thermometry network of FIG. 5 in accordance with an embodiment of the present disclosure.
Figure 7:
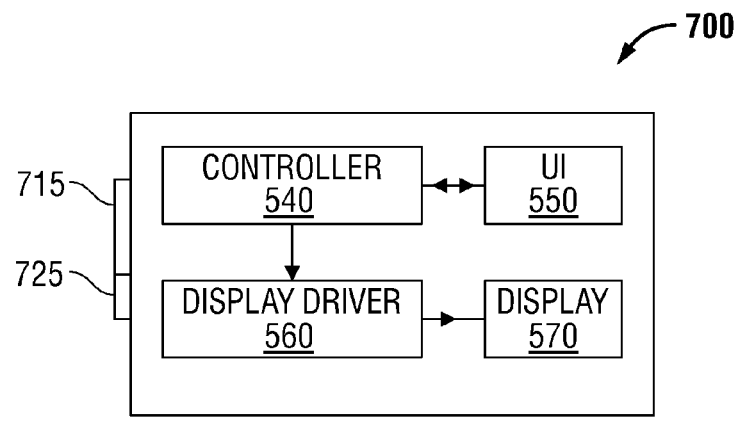
FIG. 7 is a block diagram of a radiometer controller module according to the split configuration of the microwave thermometry network of FIG. 5 in accordance with an embodiment of the present disclosure.

The microwave thermometry network module 500 of FIG. 5 may all reside in the same physical location within the microwave ablation system or the various elements of the microwave thermometry network module 500 may be located at different locations within the microwave ablation system, i.e., a split configuration. FIGS. 6 and 7 illustrate a split configuration of the microwave thermometry network module 500 of FIG. 5. FIG. 6 is a measurement module 600 that includes components of the microwave thermometry network module 500 associated with the measurement of a noise temperature signal, which is coupled from the microwave transmission line 675 via the coupling network 530.

The coupling network 530 may be implemented by any known microwave coupling scheme, such as the directional coupler 300 of FIG. 3A, the switch 350 of FIG. 3B, the T-network 375 of FIG. 3C, a band pass filter, or a diplexer. The filter 520 constrains the coupled microwave energy entering the radiometer 510 to that which represents the thermal parameter of interest. The filter 520 performs frequency spectrum selection and the radiometer 510 includes a detector, e.g., the detector 432 of FIG. 4B, for detecting the noise temperature signal.

The measurement module 600 also includes connectors for interfacing with other components of the microwave ablation system. The measurement module 600 includes data bus connectors 615a and 615b through which a noise temperature signal may be transmitted to other components of the microwave ablation system connected to the measure module 600 via the data bus connectors 615a and 615b. The measurement module 600 also includes an input power supply line connector 625b for receiving power from another component of the microwave ablation system that is connected to the input power supply line connector 625b, and an output power supply connector 625a through which power is provided to still another component of the microwave ablation system connected to the power supply line connector 625a.

The measurement module 600 further includes transmission line connectors 680a and 680b that are connected to both ends of a transmission line 675 of the thermometry network module. The transmission line connectors 680a and 680b are used for connecting the measurement module 600 between components of the microwave ablation system so that the coupling network 530 can obtain a portion of the microwave signal transmitted by the microwave generator 1000 to the microwave applicator 800. For example, as illustrated in FIG.

17A, the measurement module 600 may be directly connected between the microwave generator 1000 and the microwave applicator 800. Alternatively, the measurement module 600 may be directly connected to the microwave applicator 800, but indirectly connected to the microwave generator 1000 by connecting to the microwave cable 900 which, in turn, is connected to the microwave generator 1000.

FIG. 7 illustrates the control module 700 of the split configuration of the microwave thermometry network module 500 of FIG. 5. The control module 700 includes elements associated with the "smarts" of the microwave thermometry network module 500 and the user interface (UI) electronics. The "smarts" include the controller 540, which receives temperature measurements, e.g., a noise temperature signal in digital form, from the radiometer 510 via a data bus connector 715 and reacts to the temperature information by controlling the microwave output to achieve a desired system response. The controller 540 may communicate with the microwave generator 1000 via the data bus connector 715 in a manner which improves radiometer 510 performance and accuracy. For example, the controller 540 may control the microwave generator 1000 to pulse the high-power microwave therapeutic energy so that the radiometer can take noise temperature measurements between the pulses, as described in more detail below.

The controller 540, which is coupled to a user interface 550, may alert the user to the thermal status, e.g., a displayed temperature value, or halt certain system functions, e.g., halt the MW power output, when limits or values are reached, such as a targeted tissue temperature or microwave applicator temperature limit for safety or for device robustness when, for example, any component of the microwave ablation system is misused. The controller 540 also includes a power supply line connector 725 for receiving power from another module of the microwave ablation system. For example, the power supply line connector 725 may connect to the power supply line connector 1025b of the microwave generator 1000 of FIG. 10 to receive power from the power distribution unit 1045 of the microwave generator 1000.

In general, the microwave thermometry network modules 500, 600, and 700 of FIGS. 5-7, respectively, may be powered by a regulated power supply that is provided by one of the components of the microwave ablation system connected to the network modules. For example, the microwave thermometry network modules 500, 600, and 700 may receive power from the power supply 1050 and the power regulator 1040 of the microwave generator 1000. Alternatively, these microwave thermometry network modules 500, 600, and 700 may be powered by their own power supply and power regulation circuitry, e.g., battery, solar, or mains supply.

Figure 8:
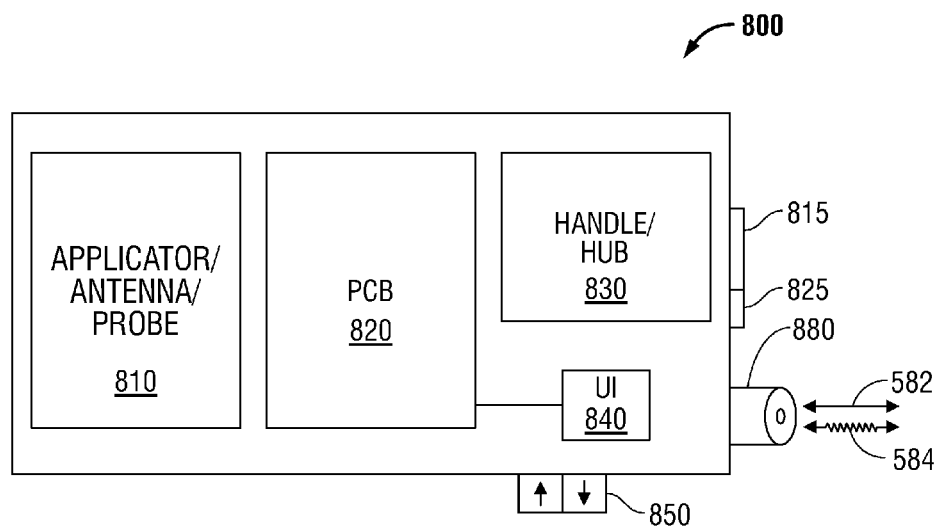
FIG. 8 is a block diagram of a microwave applicator of the microwave ablation system of FIG. 1 in accordance with an embodiment of the present disclosure.

FIG. 8 is a block diagram of a microwave applicator 800 which delivers microwave therapeutic energy to tissue to treat a disease or undesirable medical condition associated with the tissue. The microwave applicator 800 includes a probe or antenna 810 for delivering microwave energy, an applicator circuit 820, a user interface 840, a handle or hub 830, input and output fluid cooling and buffering ports 850, a data bus connector 815, a power supply line connector 825, and a transmission line connector 880. The antenna 810 receives a microwave signal via the transmission line connector 880.

The applicator circuit 820 may include a thermocouple buffer, a microwave activation switch, and/or memory (e.g., an EEPROM) storing device identification information. The thermocouple buffer converts voltage of a thermocouple (e.g., the thermocouples 2001, 2002, and 2004 of FIG. 20) into a buffered voltage representative of the thermocouple voltage, which is less sensitive to interference. The device identification information can be used by the microwave generator, e.g., the microwave generator 1000 of FIG. 10, to ensure that only properly identified microwave applicators 800 are connected to the microwave generator. In addition, the memory may store operating parameters of the microwave applicator 800 (e.g., time, power, and dosage limits) and information regarding the usage of the microwave applicator 800. Usage monitoring may enable limiting re-use of the microwave applicator 800 beyond a single use of the device or a certain number of activations.

The microwave activation switch is connected to a user-selectable activation button in the user interface 840. When a user selects the activation button, the microwave activation switch is closed to allow a microwave signal to propagate to the antenna 810 of the microwave applicator 800. The applicator circuit 820 is connected to the data bus connector 815 so that it can communicate with devices of the microwave ablation system that connect to the data bus connector 815. For example, the applicator circuit 820 may provide device identification information to a microwave generator connected to the data bus connector 815. The applicator circuit 820 also receives power via the power supply line connector 880.

The input and output cooling and buffering ports 850 connect to a fluid system (not shown) that provides cooling fluid to the antenna 810 to control the size and shape of an ablation volume. The cooling fluid may include dielectric materials to control the transfer of power to the tissue. The fluid system may include a fluid reservoir, a fluid pump for pumping cooling fluid through the input and output cooling and buffering ports 850, tubing for carrying the cooling fluid, and sensors (not shown). An example of a fluid system is described in detail in commonly assigned U.S. patent application Ser. No. 12/566,299, which is incorporated herein by reference.

Figure 9:
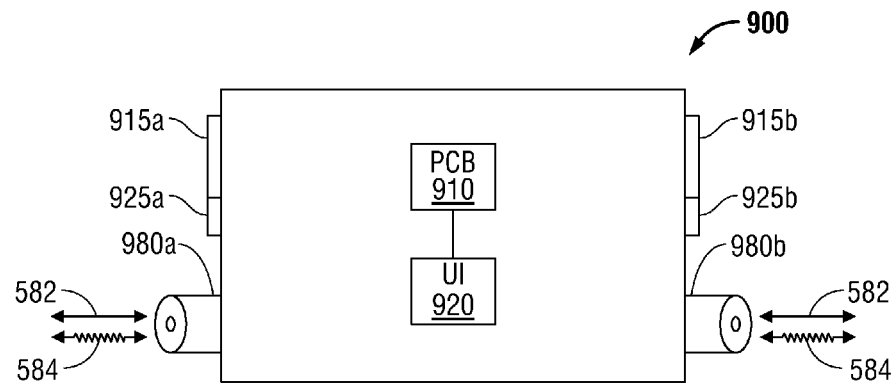
FIG. 9 is a block diagram of a cable module of the microwave ablation system of FIG. 1 in accordance with an embodiment of the present disclosure.

FIG. 9 is a block diagram of a cable 900 for carrying the high power microwave signal to the microwave applicator 800. The cable 900, which may be a reusable cable, includes cable circuitry 910, a user interface 920 which is connected to the cable circuitry 910, data bus connectors 915a and 915b, power supply line connectors 925a and 925b, and transmission line connectors 980a and 980b. The connectors 915a, 915b, 925a, 925b, 980a, and 980b may be configured to connect to corresponding connectors of any component of the microwave ablation system such as the microwave thermometry network module 500, the microwave applicator 800, the microwave generator 1000.

As described below, the microwave thermometry network module 500 may be integrated into a reusable cable. Like the applicator circuitry 820 of FIG. 8, the cable circuitry 910 may support device identification, thermocouple buffering, and/or microwave activation. The cable circuitry 910 may also communicate with other components in the microwave ablation system via the data bus connectors 915a and 915b.

Figure 10:
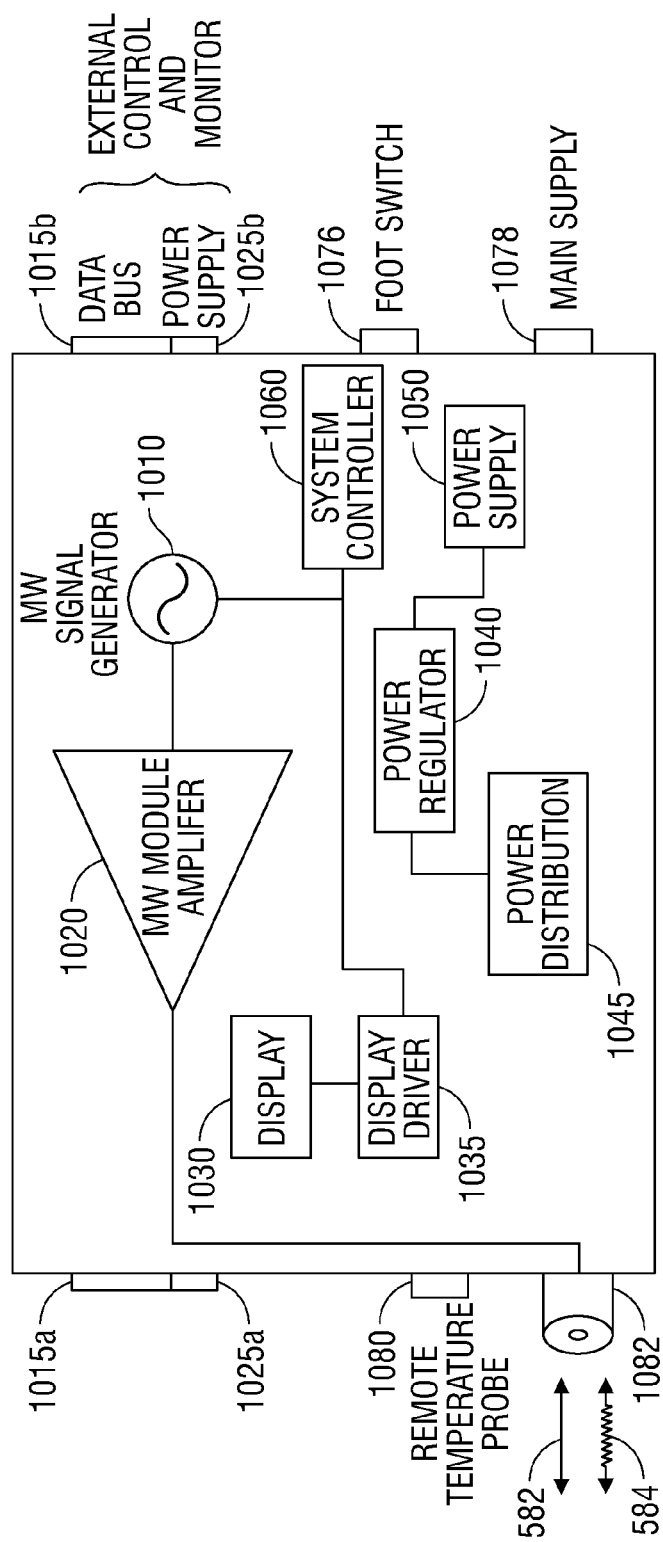
FIG. 10 is a block diagram of a microwave generator of the microwave ablation system of FIG. 1 in accordance with an embodiment of the present disclosure.

FIG. 10 is a block diagram of a microwave generator 1000 according to embodiments of the present disclosure. The microwave generator 1000 includes a microwave signal generator 1010, a microwave module amplifier 1020 coupled to the output of the microwave signal generator 1010, a transmission line connector 1082 coupled to the output of the microwave module amplifier, and a coaxial cable connector assembly for connecting to another cable, which is coupled to the microwave applicator 800 of FIG. 8. The microwave signal generator 1010 generates a microwave signal, which is amplified by the microwave module amplifier 1020 to produce a high power microwave signal 582. The high power microwave signal 582 is output from the microwave generator 1000 via the transmission line connector 1082. As described herein, the transmission line connector 1082 connects to another component of the microwave ablation system, e.g., the cable 900 of FIG. 9, which carries the high power microwave signal 582 to a microwave applicator, e.g., the microwave applicator 800 of FIG. 8.

The microwave generator 1000 further includes a power system for powering the various components of the microwave ablation system. The power system includes a power supply 1050, a power regulator 1040, and a power distribution circuit 1045. The power supply 1050 converts alternating current (AC) from the mains supply connector 1078, which may connect to a standard AC outlet via a mains supply line (not shown), to direct current (DC). The power regulator 1040 converts the DC output from the power supply 1050 into regulated DC of various power levels.

The power regulator 1040 provides low power DC to the microwave signal generator 1010, the system controller 1060, and the power distribution circuit 1045. The power distribution circuit 1045, in turn, provides power to power supply line connectors 1025a and 1025b for providing power to components that connect to the microwave generator 1000. In particular, the power distribution circuit 1045 provides low power DC to external control and monitoring circuitry, such as the control module 700 of FIG. 7, via the power supply line connector 1025b. The power distribution circuit 1045 also provides low power DC to the microwave applicator 800 and other components of the microwave ablation system that connect directly or indirectly to the power supply line connectors 1025a and 1025b. The power regulator 1040 also provides high power DC to the microwave module amplifier 1020, which outputs a high power microwave signal 582 via the transmission line connector 1082.

The system controller 1060 is connected to the microwave signal generator 1010 to control the phase, frequency, and other parameters of the microwave signal 582 output from the microwave module amplifier 1020. The system controller 1060 is also connected to the data bus connectors 1015a and 1015b to enable communications between the microwave generator 1000 and various components of the microwave ablation system that connect to the microwave generator 1000, including the microwave thermometry network module 500 of the present disclosure. In embodiments, the system controller 1060 may receive feedback signals through the data bus connectors 1015a and 1015b to control the parameters of the high power microwave signal 582. For example, the controller 540 of the microwave thermometry network module 500 of FIG. 5 could control the high power microwave signal 582, e.g., by pulsing, halting, or varying the high power microwave signal 582.

The microwave generator 1000 also includes input and output devices including a display 1030 and a display driver 1035. The system controller 1060 controls the display driver 1035 to display information regarding operation of the microwave ablation system on the display 1030. The microwave generator 1000 also includes a footswitch connector 1076 for connecting to a footswitch controller. The system controller 1060 receives command signals from the footswitch controller for controlling the output from the microwave generator 1000.

The microwave generator 1000 also incorporates a temperature probe connector 1080 for connecting to a remote temperature probe (not shown). As described below, the remote temperature probe may be used to measure the temperature of the patient to obtain patient temperature measurements for calibrating the temperature measurements of the microwave thermometry network module 500. The temperature probe connector 1080 may also accept a T-type thermocouple arrangement. The controller of the microwave thermometry network module 500 could condition the radiometer output into a T-type signal. This feature could be used to display temperature to the user via a front panel 7-segment display.

FIGS. 11A-11C and 12A-12D illustrate different example configurations of the microwave ablation system using the microwave thermometry network module 500 of FIG. 5. As shown in FIGS. 11A-11C and 12A-12D, the thermometry network module 500 is disposed along the microwave transmission path between the microwave generator 1000 and the microwave applicator 800.

Figure 11A:
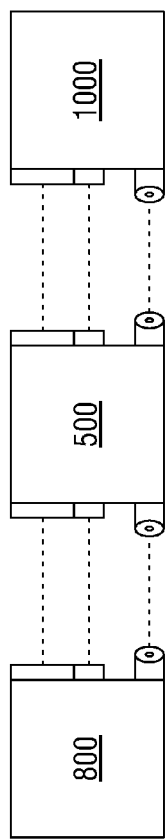
FIGS. 11A-11C illustrate microwave ablation system configurations in which the microwave thermometry network module is a standalone component in accordance with embodiments of the present disclosure.
Figure 11B:
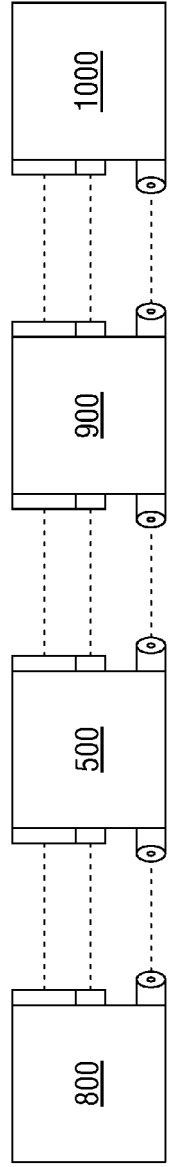
Figure 11C:
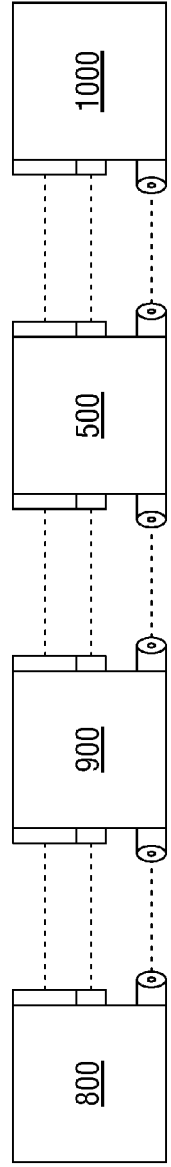

FIGS. 11A-11C illustrate configurations in which the microwave thermometry network module 500 is a standalone component in a microwave ablation system that is divided into three or four separate components that are connectable to each other. In FIG. 11A, the microwave thermometry network module is connectable between the microwave applicator and the microwave generator module. The configuration of FIG. 11A may be used in a portable microwave ablation system where, for example, the microwave generator 1000 and the microwave thermometry network module 500 are disposed in a handle of the portable microwave ablation system, the microwave applicator 800 is connectable to the handle, and the microwave thermometry network module 500 is connectable to the handle so that the microwave thermometry network module 500 connects between the microwave applicator 800 and the microwave generator 1000.

In FIG. 11B, the microwave thermometry network module is connectable to a distal end of the cable 900 and to the microwave applicator 800. In FIG. 11C, the microwave thermometry network module 500 is connectable to the proximal end of the cable 900 and to the microwave generator 1000.

Figure 12A:
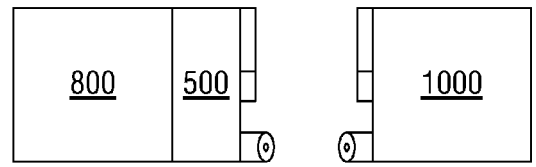
FIGS. 12A-12D illustrate microwave ablation system configurations in which the microwave thermometry network module is integrated into any one of the components of the microwave ablation system in accordance with embodiments of the present disclosure.
Figure 12B:
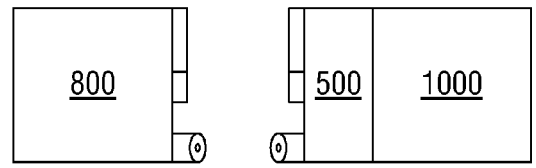
Figure 12C:
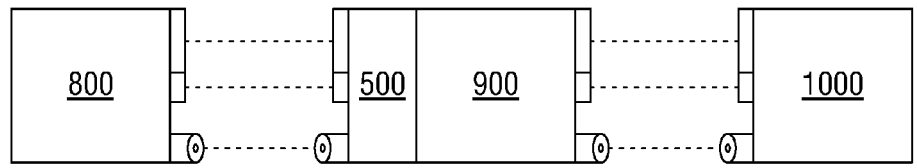
Figure 12D:
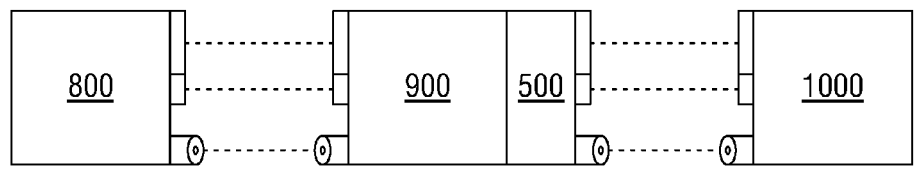

FIGS. 12A-12D illustrate configurations in which the microwave thermometry network module 500 is integrated into any one of the components of a microwave ablation system that is divided into two or three separate components that are connectable to each other. In FIG. 12A, the measurement module 600 is also standalone component that is connectable between the microwave applicator 800 and the microwave generator 1000. In FIG. 12A, the microwave thermometry network module 500 is integrated into the microwave applicator 800. In FIG. 12B, the microwave thermometry network module 500 is integrated into the microwave generator 1000. In FIG. 12C, the microwave thermometry network module 500 is integrated into the connector assembly at the distal end of the cable 900. In FIG. 12D, the microwave thermometry network module 500 is integrated into the connector assembly at the proximal end of the cable 900.

Figure 13:
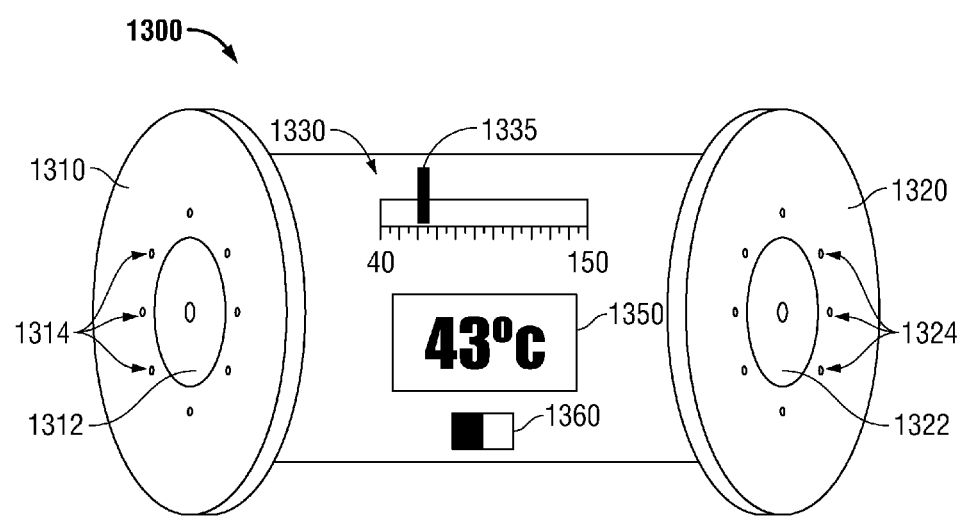
FIG. 13 is a perspective view of a cable incorporating a radiometer controller in accordance with an embodiment of the present disclosure.

FIG. 13 is a perspective view of a standalone microwave thermometry network module 1300 that incorporates the circuitry of the microwave thermometry network module 500 shown in FIG. 5. The microwave thermometry network module 1300 includes a connector 1320 at its proximal end for connecting directly to the microwave generator 1000, as shown in the configurations of FIGS. 11A and 11C, or for connecting to the microwave cable 900, as shown in the configuration of FIG. 11B.

The first connector integrates a concentric data bus connector 1324 with a coaxial connector 1322 to enable communications between a thermometry network module 1300 and a microwave generator. The thermometry network module 1300 includes a display 1350 and a user interface having a selector 1330 and a switch 1360. The display 1350 displays the temperature that is determined, for example, by the controller 540 based on thermal measurements obtained by the radiometer 510 of the thermometry network module 500 of FIG. 5.

The selector 1330 includes a knob 1335 that allows a user to select a temperature limit at which microwave power is shutoff. The controller 540 may send a message to the microwave generator 1000 to shut off when the controller 540 determines that the measured temperature exceeds the selected temperature limit. Alternatively, the cable may include a switch (not shown) that opens when the controller 540 determines that the measured temperature exceeds the selected temperature limit to disconnect microwave power from the microwave applicator. The switch 1360 allows a user to turn on or shut off power to the microwave applicator 800. In some embodiments, the display 1350 is a touch screen display and the selector 1330 and/or the switch 1360 are implemented as a "virtual" selector and/or switch in the touch screen display. In other embodiments, the selector 1330 and/or the switch 1360 are implemented as a physical selector and/or switch.

The microwave thermometry network module 1300 includes another connector 1310 at its distal end for connecting directly to the microwave applicator 800, as shown in the configurations of FIGS. 11A and 11B, or for connecting to the microwave cable 900, as shown in the configuration of FIG. 11C. Similar to connector 1320, connector 1310 integrates a concentric data bus connector 1314 with a coaxial connector 1312 to enable communications between the thermometry network module 1300 and the microwave applicator 800. The connector 1310 may be configured to twist to lock or unlock connection with a microwave applicator.

Figure 14:
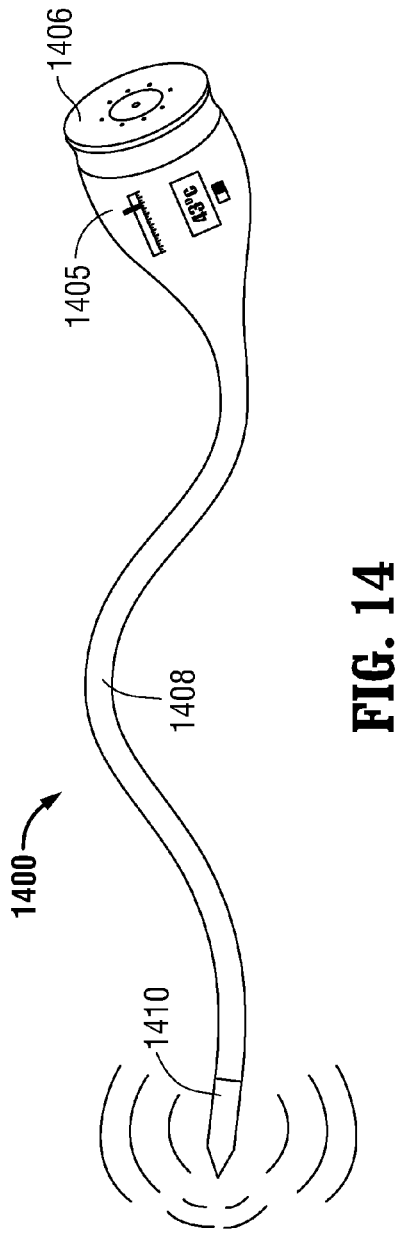
FIG. 14 is a perspective view of a microwave applicator including a radiometer controller in accordance with an embodiment of the present disclosure.

FIG. 14 is a perspective view of a microwave applicator 1400 that incorporates the microwave thermometry network module 500 of FIG. 5 into the microwave applicator's connector assembly 1405. The connector assembly 1405 is connected to a probe 1408 having a radiating portion 1410. Similar to FIG. 13, the connector assembly 1405 includes a display that displays temperature measurements and a user interface that allows a user to change temperature settings and to shutoff microwave signals being provided to the probe 1408 to cause the radiating portion 1410 to emit microwave radiation.

The connector assembly 1405 includes a connector 1406 similar to connectors 1310 and 1320 of FIG. 13 that is configured to connect directly to the microwave generator 1000, as shown in the configuration of FIG. 12A, or to connect to the microwave generator 1000 via a microwave cable. Temperature measurement data may be transmitted to the microwave generator 1000 via the data bus of the connector 1406.

Figure 15:
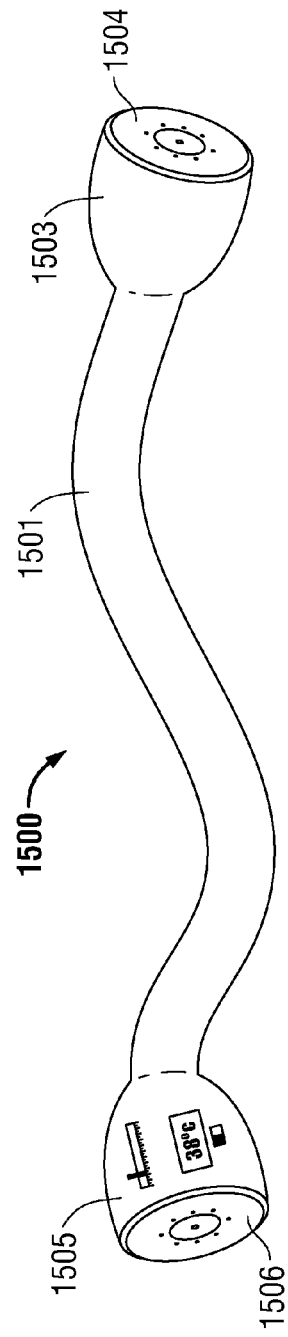
FIG. 15 is a perspective view of a microwave cable including a radiometer controller in accordance with an embodiment of the present disclosure.
Figure 16A:
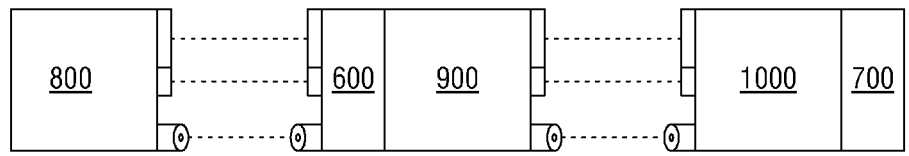
FIGS. 16A-16D illustrate microwave ablation system configurations in which the radiometer controller module is integrated into the microwave generator of the microwave ablation system in accordance with embodiments of the present disclosure.
Figure 16B:
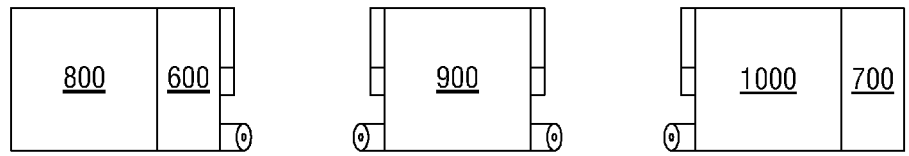
Figure 16C:
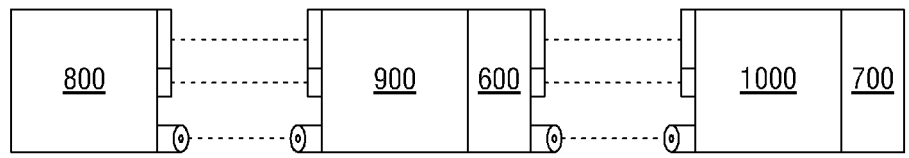
Figure 16D:
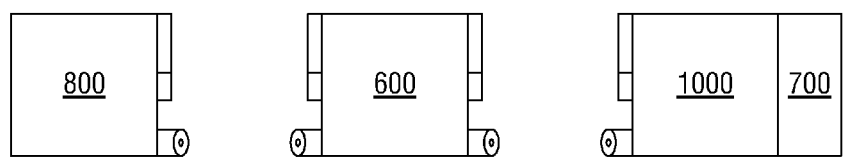

FIG. 15 is a perspective view of a microwave cable assembly 1500 including coaxial cable 1501, a connector assembly 1503 attached to the proximal end of the coaxial cable 1501 and a connector assembly 1505 attached to the distal end of the coaxial cable 1501. In this embodiment, the components of the microwave thermometry network module 500 of FIG. 5 are incorporated into connector assembly 1505 of the microwave cable assembly 1500 as shown in the configuration of FIG. 12C. Similar to the connector assembly 1405 of FIG. 14, the connector assembly 1505 includes a display that displays temperature measurements and a user interface that allows a user to change temperature settings and to shutoff microwave signals being carried by the microwave cable assembly 1500.

Alternatively, the microwave thermometry network module 500 may be incorporated into the connector assembly 1503 at the proximal end of the microwave cable assembly 1500 as shown in the configuration of FIG. 12D. The connector assemblies 1503 and 1505 include connectors 1504 and 1506, respectively, similar to the connectors 1310 and 1320 of FIG. 13. As shown in the configuration of FIG. 12C, connector 1504 is configured to connect directly to the microwave generator 1000 and connector 1506 is configured to connect directly to the microwave applicator 800. In this configuration, temperature data may be transmitted to the microwave generator 1000 via the data bus of connector 1504.

Incorporating the components of the microwave thermometry network module 500 into a microwave cable minimizes the number of changes that need to be made to the microwave applicator 800 and/or the microwave generator 1000 to incorporate microwave thermometry according to the present disclosure. In some cases, the circuitry of the system controller 1060 is simply reconfigured to receive temperature data from the controller 540 of the microwave thermometry network module 500.

FIGS. 16A-16D and 17A-17D illustrate different example configurations of the microwave ablation system using the split configuration of the microwave thermometry network module as illustrated by FIGS. 6 and 7. As shown in 16A-16D and 17A-17D, the measurement module 600 is disposed along the microwave transmission line between the microwave generator 1000 and the microwave applicator 800. The control module 700 may be disposed anywhere within the ablation system.

FIGS. 16A-16D illustrate configurations in which the control module 700 is integrated into the microwave generator 1000 and the microwave ablation system is divided into three separate components that are connectable to each other. In FIG. 12A, the measurement module 600 is integrated into the distal end of the cable 900. In FIG. 12B, the measurement module 600 is integrated into the microwave applicator 800. In FIG. 12C, the measurement module 600 is connectable to the proximal end of the cable 900. In FIG. 12D, the measurement module is a standalone component that is connected between the microwave applicator and the microwave generator. The configuration of FIG. 12D may be used in a portable microwave ablation system where, for example, the microwave generator 1000 and the control module 700 are disposed in a handle of the portable microwave ablation system, the microwave applicator 800 is connectable to the handle, and the measurement module 600 is connectable to the handle so that the measurement module 600 connects between the microwave applicator 800 and the microwave generator 1000.

Figure 17A:
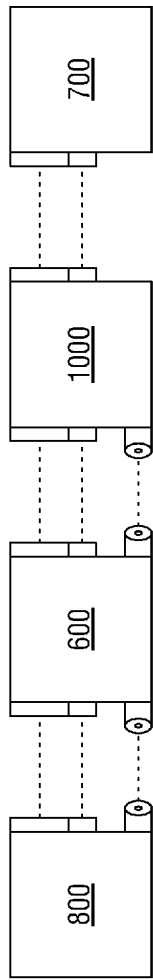
FIGS. 17A-17D illustrate microwave ablation system configurations in which the radiometer controller module is configured to removably connect to the microwave generator of the microwave ablation system in accordance with embodiments of the present disclosure.
Figure 17B:
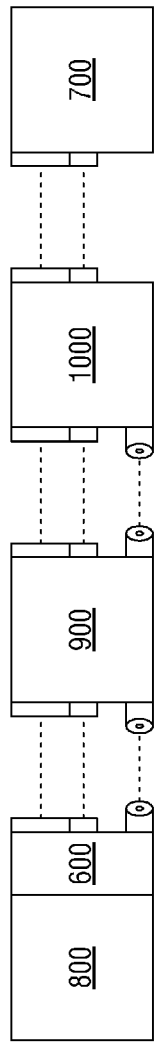
Figure 17C:
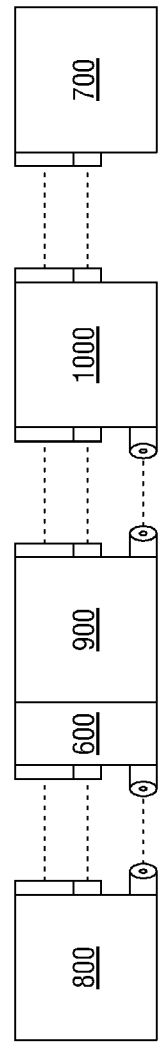

FIGS. 17A-17D illustrate configurations in which the control module 700 is a standalone component that is connectable to the microwave generator 1000 and the microwave ablation system is divided into three or four separate components that are connectable to each other. In FIG. 17A, the measurement module 600 is also standalone component that is connectable between the microwave applicator 800 and the microwave generator 1000. In configuration 17B, the measurement module 600 is integrated into the microwave applicator 800. In FIG. 17C, the measurement module 600 is integrated into the distal end of the cable 900.

Figure 17D:
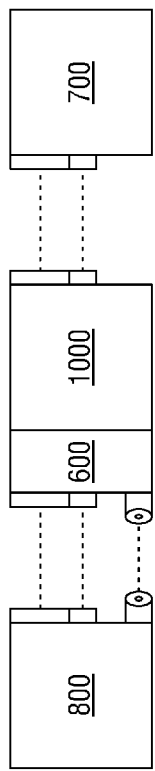

In FIG. 17D, the microwave ablation system is divided into three separate components in which the measurement module 600 is integrated into the microwave generator 1000. Like the configuration of FIG. 16D, the configuration of FIG. 17D may be used in a portable microwave ablation system where, for example, the microwave generator 1000 and the measurement module 600 are disposed in a handle of the portable microwave ablation system, the microwave applicator 800 is connectable to the handle so that the microwave applicator 800 connects to the measurement module 600, and the control module 700 is connectable to the handle so that the control module 700 connects to the microwave generator 1000.

Figure 18:
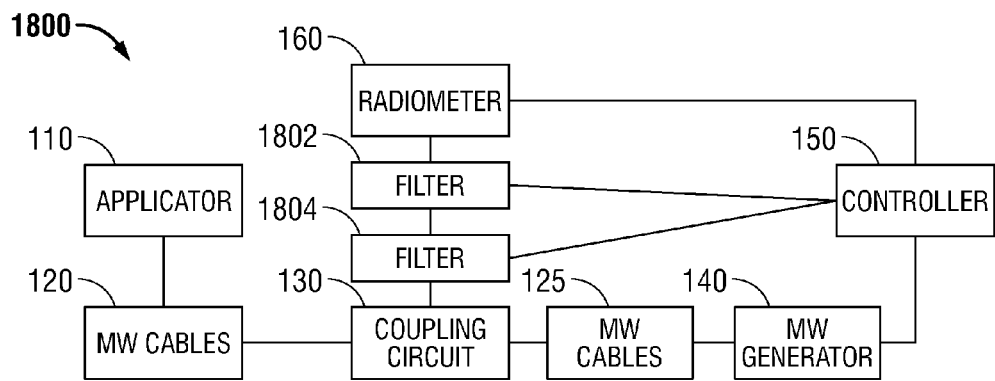
FIG. 18 is a block diagram of a microwave ablation system in accordance with other embodiments of the present disclosure.

FIG. 18 is a block diagram of a microwave ablation system 1800 in accordance with other embodiments of the present disclosure. The microwave ablation system 1800 is the same as the microwave ablation system 100 shown in FIG. 1 except that the microwave ablation system 1800 includes filters 1802 and 1804, which are controlled by the controller 150. The first filter 1802 may separate the noise temperature signal from the high power microwave signal. The second filter 1804 may then extract the noise temperature of the tissue and the noise temperature of the transmission network from the noise temperature output from the first filter 1802.

The controller 150 may provide tuning, gating, and other signals to control the manner in which the first filter 1802 and the second filter 1804 filter the microwave energy provided by the coupling circuit. The second filter 1804 may be further configured to separate out components of the transmission network noise temperature or the tissue noise temperature. For example, different components of the transmission network may produce noise temperature signals at different frequencies. The second filter 1804 may employ frequency domain techniques to determine the noise temperature of each of the components of the transmission network by analyzing the noise temperature signals at different frequencies. The second filter 1804 may alternatively employ both time domain and frequency domain techniques to isolate noise temperature signals from intentional sources, such as the microwave generator 1000, from other noise temperature sources, such as the cables and the tissue.

In some situations, the noise temperature from the transmission network, e.g., the microwave applicator and/or the microwave cable, may obscure the noise temperature of the tissue. To overcome this issue, the microwave signal output from the microwave generator may be turned off for an off period and the radiometer may monitor temperature during this off period. Additionally, the transmission network may be cooled rapidly, either through ambient cooling or active fluid cooling, to allow for the separation of the transmission network noise temperature and the tissue noise temperature. Once the transmission network has cooled sufficiently, the radiometer may measure the temperature to obtain the noise temperature of the tissue.

Figure 19:
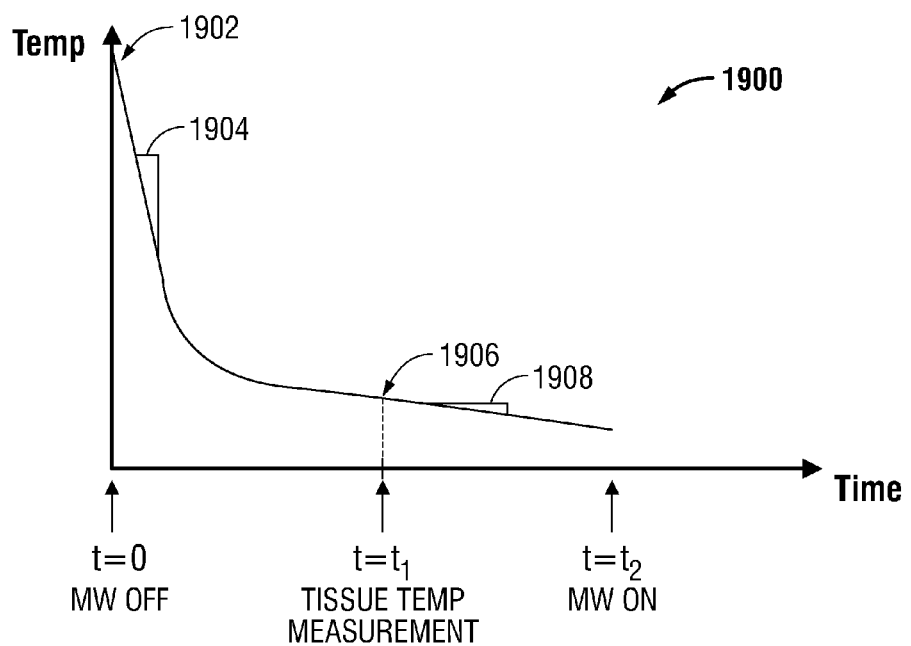
FIG. 19 is a block diagram of a microwave applicator that incorporates thermocouples for measuring temperatures that are used to control the radiometer in accordance with embodiments of the present disclosure.

As illustrated by the graph 1900 of FIG. 19, when the microwave energy source is turned off at time t=0, the magnitude of the noise temperature 1902 represents a combination of the noise temperatures of the transmission network and the tissue. As the transmission network is cooled, either through ambient cooling or active fluid cooling, the magnitude of the noise temperature drops rapidly as illustrated by the steep slope 1904 of the noise temperature curve. Once the transmission network cools down to a point where the magnitude of the noise temperature represents the tissue temperature 1906, e.g., at time t=$t_1$, the radiometer may measure the noise temperature to obtain the noise temperature of only the tissue. The gradual slope 1908 of the temperature curve is due to the tissue temperature dropping. Then, the microwave signal turns back on at time t=$t_2$ to continue tissue treatment.

The noise temperature of the transmission network may be obtained by first measuring the temperature immediately after the generator turns off, e.g., at time t=0 in the graph 1900 of FIG. 19. This temperature represents the combined temperatures of the transmission network and the tissue. Thus, to obtain the temperature of the transmission network, the tissue noise temperature is subtracted from the noise temperature measured immediately after the generator turns off.

The flow of cooling fluid could be shut off at time t=$t_2$ instead of turning the microwave signal on, which would result in the noise temperature curve rising as the cooling fluid temperature rises to the tissue temperature. This rise in cooling fluid temperature would roll-off as the cooling fluid temperature equalizes to the tissue temperature. This roll-off point could further be used to indicate tissue temperature. The microwave signal would then be turned on at time t=$t_3$ if the desired temperature had not been achieved.

Figure 20:
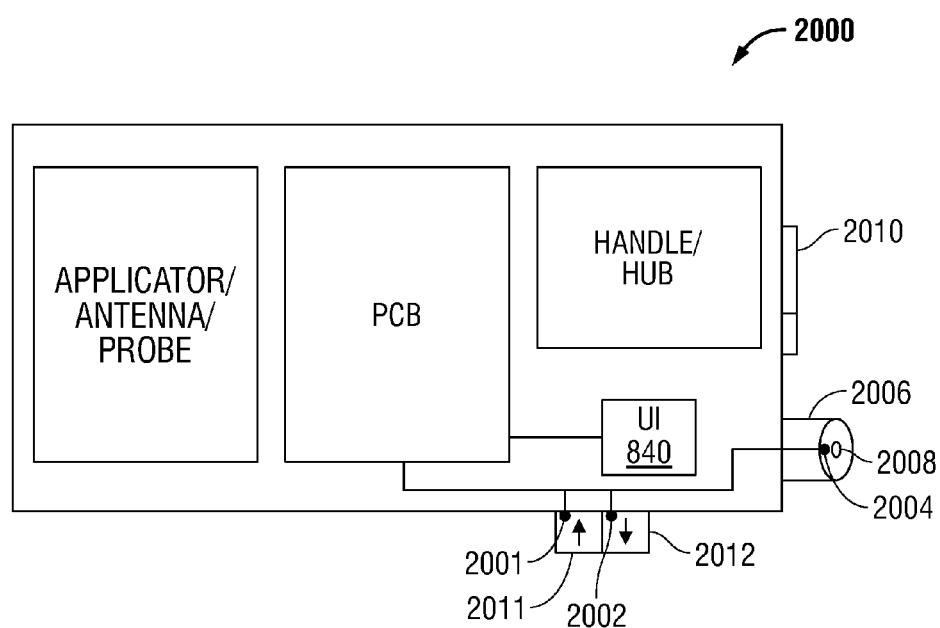
FIG. 20 is a graph illustrating the timing of temperature measurements by the radiometer in accordance with some embodiments of the present disclosure.

FIG. 20 shows a microwave applicator 2000 having thermocouples for taking temperature measurements of the transmission network and the cooling fluid in order to determine when the magnitude of the temperature represents the tissue temperature. The microwave applicator 2000 includes a first thermocouple 2001 positioned at the fluid inlet 2011 for measuring the temperature of the fluid entering the fluid inlet 2011 and a second thermocouple 2002 positioned at the fluid outlet 2012 for measuring the temperature of the fluid exiting the fluid outlet 2012. The microwave applicator 2000 further includes a third thermocouple 2004 positioned at a suitable location along the transmission network to accurately measure a representative temperature of the transmission network. For example, the third thermocouple 2004 may be positioned near the inner conductor 2008 of a coaxial cable connector 2006 of the transmission network.

The thermocouples 2001, 2002, and 2004 are used to measure the temperature of the cooling fluid and the transmission network in order to determine when the noise temperature measured by the radiometer represents the tissue temperature. These tissue measurements may be transmitted to a controller, e.g., the controller 540 of the thermometry network module 500 of FIG. 5, outside of the microwave applicator 2000 via the communications interface 2010 so that the controller can control the radiometer measurements. Specifically, when the controller determines that the temperature of the transmission network as measured by thermocouple 2004 is the same as the temperature of the cooling fluid as measured by thermocouples 2001 and 2002, the transmission network no longer contributes to the noise temperature. The tissue may be the sole contributor to the noise temperature at this point in time. Thus, the controller may control the radiometer to measure the noise temperature at this point in time to obtain the tissue noise temperature.

Alternatively, the controller may control the radiometer to measure the noise temperature to obtain tissue temperature measurements when the temperature of the cooling fluid flowing through the inlet (as measured by thermocouple 2001) is the same as the temperature of the cooling fluid flowing through the outlet (as measured by thermocouple 2002). As another alternative, the controller may control the radiometer to measure the noise temperature when the slope of the temperature curve settles to the tissue temperature slope 1908 of FIG. 19 as described in more detail below.

Figure 21A:
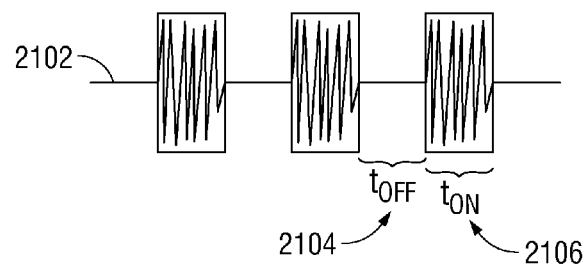
FIGS. 21A and 21B are timing diagrams illustrating the timing of temperature measurements by the radiometer in accordance with other embodiments of the present disclosure.
Figure 21B:
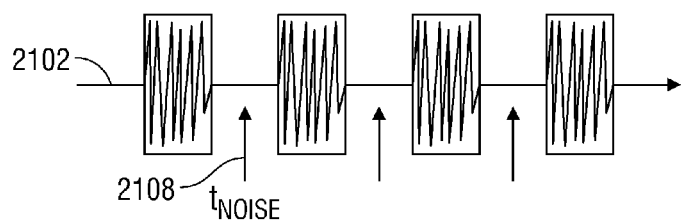

FIGS. 21A and 21B are timing diagrams illustrating the timing of temperature measurements by the radiometer in accordance with other embodiments of the present disclosure. As illustrated in FIG. 21A, the microwave signal generated by the microwave generator may be a pulse-width modulated (PWM) signal 2102 at maximum generator peak power to provide variable average power. The sum of the off time 2104 and the on time 2106 define the period t of the PWM signal 2102, where 1/t is the PWM modulation frequency, which may be between 1 kHz and 100 kHz, and the microwave frequency is between 500 MHz and 15 GHz. The average output power $P_{average}$ of the PWM signal 2102 is given by the following equation:

$$P_{average} = \frac{t_{on}}{t_{on} + t_{off}} \times P_{max},$$

where $P_{max}$ is the maximum peak power.

As shown in FIG. 21B, the radiometer according to the present disclosure may sample 2108 the noise temperature of the microwave ablation system during the off times of the microwave PWM signal. So long as the duty cycle of the PWM signal is less than 100 percent, there are off times during which the radiometer can sample the noise temperature. By sampling the noise temperature during the off times, the noise temperature signal is isolated from the high power microwave therapy energy in time.

Figure 22:
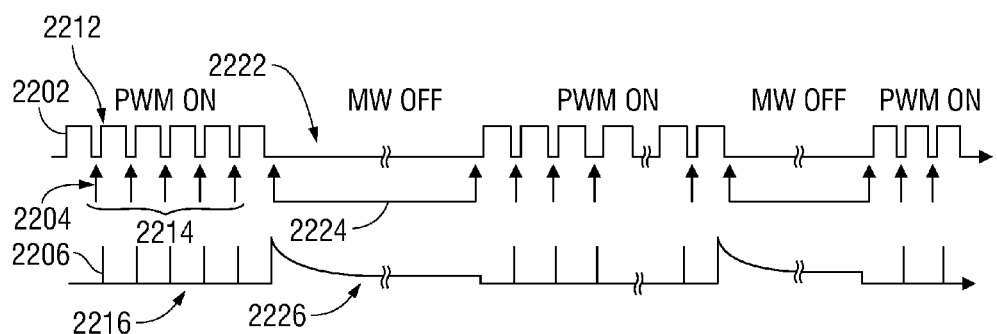
FIG. 22 is a timing diagram illustrating the timing of temperature measurements by the radiometer in accordance with yet other embodiments of the present disclosure.

In other embodiments, the microwave ablation system may additionally turn off the microwave signal for an extended period of time (e.g., 5 to 60 seconds) allowing the system to cool (either actively or passively) and allowing the radiometer to measure a time-varying noise temperature curve as described above in FIG. 19. This is illustrated by the timing diagram of FIG. 22. The controller 150 of FIG. 18 may be configured to control the microwave generator 140 to generate a microwave signal 2202 that is a pulse-width modulated (PWM) signal for a first period 2212 and to turn off the PWM signal for a second period 2222. At the same time, the controller 150 or a controller of the microwave generator 140 may vary the duty cycle of the PWM signal to vary the output power. Also, the controller 150 may control the radiometer 160 to measure noise temperature at various points 2204 along the microwave signal 2202 to obtain a noise temperature measurement signal 2206.

Specifically, the controller 150 may control the radiometer 160 to measure the noise temperature during the PWM off periods 2214 to monitor the maximum noise temperature of the microwave ablation system. The noise temperature measurements 2216 for the PWM off periods 2204 may be provided as feedback to a controller, e.g., the controller 540 of FIGS. 5 and 7, which may control the microwave signal output from the microwave generator. For example, the noise temperature measurements 2216 may be used by the controller 540 to reduce the duty cycle of the PWM signal 2212, to keep the transmission network temperatures within acceptable limits, to ensure adequate cooling of the microwave ablation system, or to prevent misuse. The controller 540 may determine whether any of the noise temperature measurements 2216 is greater than a predetermined noise temperature value, and may shut off the microwave signal or reduce the duty cycle of the PWM microwave signal if it is determined that any of the noise temperature measurements 2216 is greater than a predetermined noise temperature value.

Additionally, the radiometer may be configured to take a longer continuous sample 2224 during the second period 2222 when the microwave signal is turned off. The resulting noise temperature curve 2226 can be used to separate the various noise temperature contributions, e.g., separate the transmission network noise temperature from the tissue noise temperature, by observing the cooling behavior of the transmission network as described above. By shutting off the microwave PWM signal periodically, e.g., every 30-60 seconds, a system controller allows the transmission network and other components of the microwave ablation system to cool down and the system controller can avoid reducing the PWM signal's duty cycle in order to reduce the temperature the transmission network and other components of the system to a suitable temperature level.

If the periods during which the microwave signal is turned off 2222 are a small fraction of the PWM on time 2212, the average power delivered to the microwave applicator may be maintained high or near the maximum output power of the generator amplifier. For example, if the maximum output power $P_{max}$ is 115 W and the microwave signal off time is 5 seconds every 1 minute with a PWM signal having a 95% duty cycle, then the average microwave output power $P_{avg}$ from the generator is:

$$P_{avg} = P_{max}\left(1 - \frac{5 \text{ seconds}}{60 \text{ seconds}}\right)(0.95) \approx 0.87 P_{max} \approx 100 \text{ W}.$$

Figure 23:
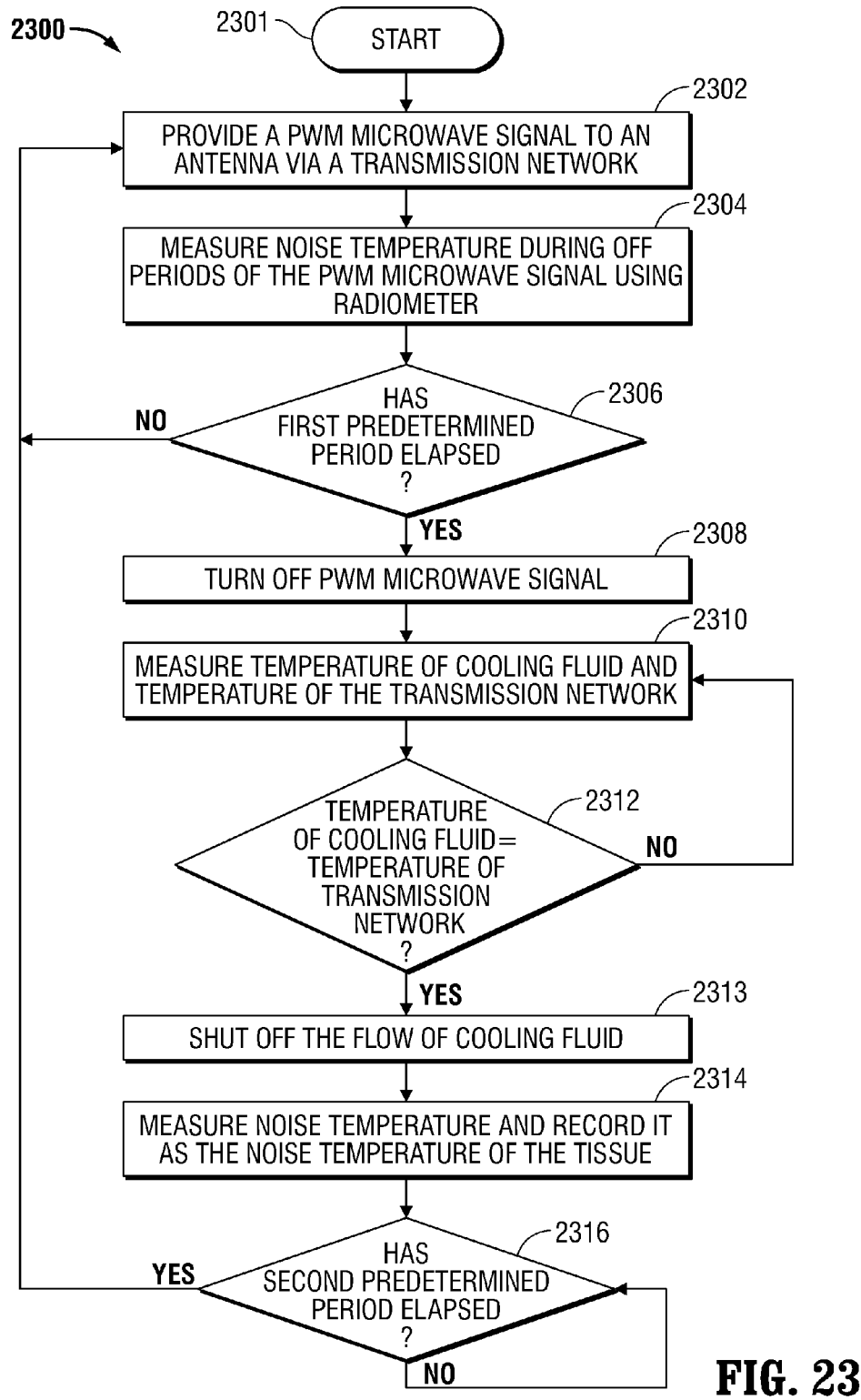
FIG. 23 is a flowchart of a method of operating the microwave ablation system according to an embodiment of the present disclosure.

FIG. 23 is a flowchart of a method 2300 for operating the microwave ablation system according to an embodiment of the present disclosure. After the method 2300 starts in step 2301, a PWM microwave signal is provided to an antenna via a transmission network in step 2302. The PWM microwave signal may be generated by a microwave generator that adjusts the duty cycle of the PWM microwave signal to obtain a power level that achieves a desired tissue effect. In step 2304, the noise temperature is measured by a radiometer during the off periods of the PWM microwave signal. In step 2306, it is determined whether a first predetermined period, during which the PWM microwave signal is provided to the antenna, has elapsed. If the first predetermined period has not elapsed, the method 2300 continues to provide a PWM signal in step 2302 and measure the noise temperature in step 2304.

If the first predetermined period has elapsed, the PWM microwave signal is turned off in step 2308, which causes the transmission network to rapidly cool by a cooling fluid from a fluid cooling system of the microwave ablation system. In step 2310, the temperature of the cooling fluid and the temperature of the transmission network are measured, e.g., by the thermocouples 2001, 2002, and 2004 of FIG. 20. In step 2312, it is determined whether the temperature of the cooling fluid is equal to or substantially equal to the temperature of the transmission network. If it is determined that the temperature of the cooling fluid is equal to or substantially equal to the temperature of the transmission network, the flow of cooling fluid is shut off in step 2313. The cooling fluid flowing around the radiator or antenna may make it difficult to measure the tissue noise temperature. Shutting off the flow of cooling fluid allows the tissue to heat the stagnant cooling fluid around the radiator or ablation zone, bringing the cooling fluid up to or near the temperature of the tissue, thus improving the accuracy of the tissue noise temperature measurement. The temperature curve of the cooling fluid (e.g., the slope and maximum roll off) after the flow of cooling fluid is shut off may be used to indicate successful completion of tissue treatment.

After shutting off the flow of cooling fluid in step 2313, the noise temperature is measured by the radiometer and is recorded as the noise temperature of the tissue, in step 2314. The noise temperature of the tissue may be measured by the radiometer a predetermined amount of time after the flow of cooling fluid has been shut off.

In step 2316, the method 2300 waits until the second predetermined period elapses before returning to step 2302 to turn on the PWM microwave signal. The second predetermined period may range between 5 seconds and 5 minutes. The second predetermined period may be varied throughout the ablation procedure. For example, a second predetermined period which is relatively short, e.g., 5 seconds, may be used several times during an ablation procedure to monitor the real-time progress of tissue treatment without significantly delaying the procedure time. During the shorter periods, the flow of fluid may be shut off for a short amount of time or the flow of fluid may not be shut off at all. Then, the second predetermined period may be longer, e.g., 5 minutes, following the ablation procedure to observe the final result of the ablation procedure and confirm that the desired result was achieved. During the longer periods, the flow of fluid may be shut off.

Figure 24:
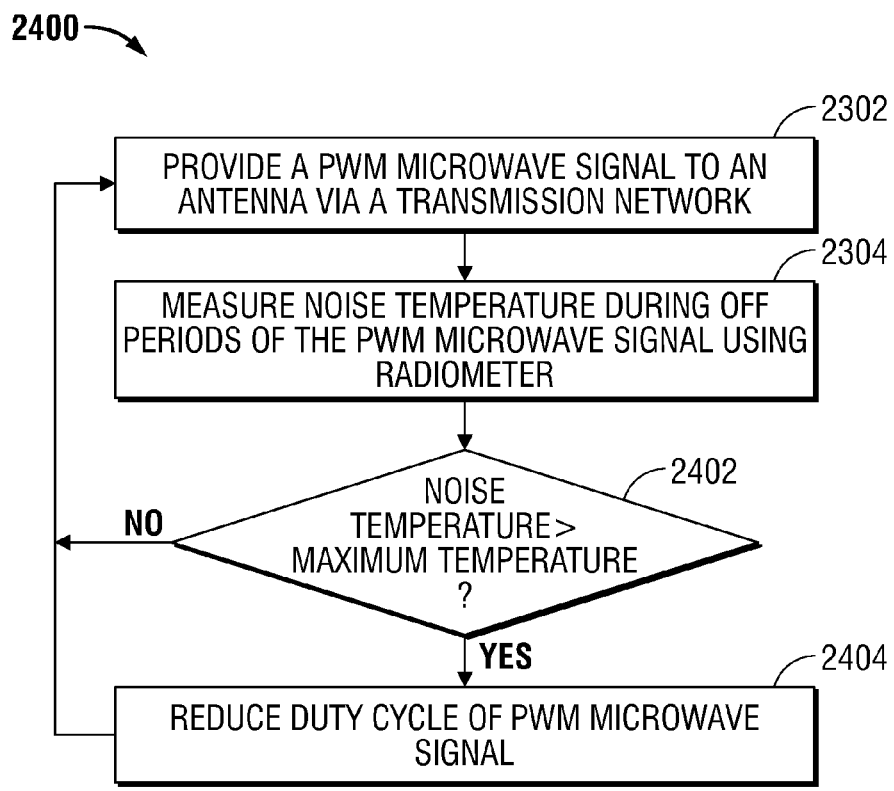
FIG. 24 is a flowchart of a method of controlling the temperature of the transmission network using radiometer measurements according to an embodiment of the present disclosure.

FIG. 24 is a flowchart of a method 2400 that may be employed together with the method of 2300 for controlling the temperature of the transmission network using the noise temperature measurements obtained by the radiometer during the off periods of the PWM microwave signal. for operating the microwave ablation system according to an embodiment of the present disclosure. As in the method 2300 of FIG. 23, a PWM microwave signal having a desired pulse width is provided to antenna via a transmission network in step 2302.

In step 2304, the noise temperature is measured by the radiometer during the off periods of the PWM microwave signal. In step 2402, it is determined whether the noise temperature as measured by the radiometer is greater than a predetermined maximum temperature. If so, the duty cycle of the PWM microwave signal is reduced in step 2404 to cause the temperature of the transmission network to decrease. Alternatively, the flow rate of the cooling fluid may be increased so as to increase the cooling rate of the transmission network. As another alternative, the PWM microwave signal may be turned off for a predetermined period to allow the transmission network to cool.

Figure 25:
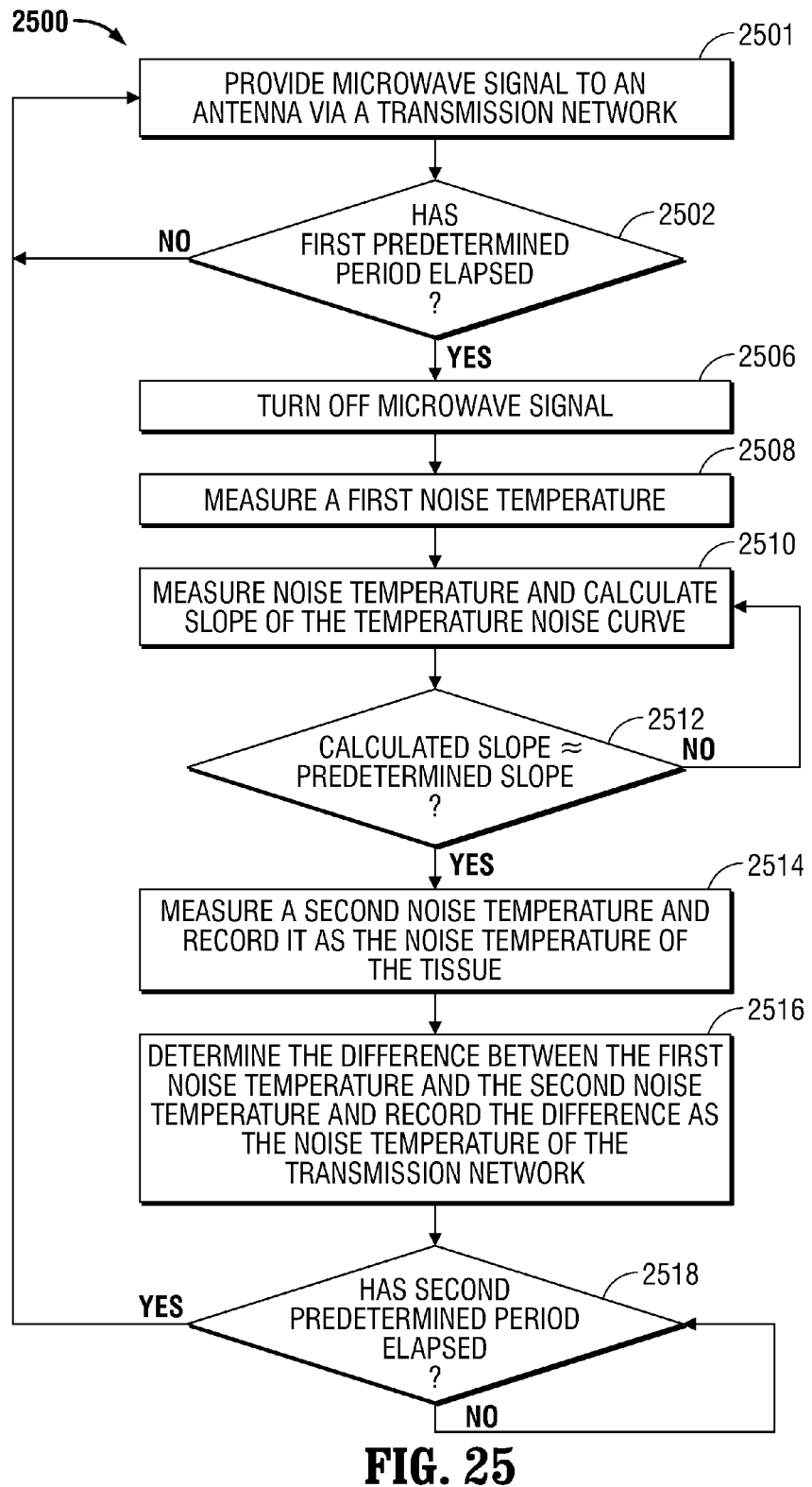
FIG. 25 is a flowchart of a method of operating the microwave ablation system according to another embodiment of the present disclosure.

FIG. 25 is a flowchart of a method of operating the microwave ablation system according to another embodiment of the present disclosure. After the method 2500 starts in step 2501, a microwave signal is provided to an antenna via a transmission network in step 2302. In step 2506, it is determined whether a first predetermined period, during which the microwave signal is provided to the antenna, has elapsed. The first predetermined period may range between 3 seconds and 1 minute or longer depending on the procedure type. For example, for large volume ablation, the first predetermined period would be longer whereas for renal devervation, this period would be longer. If the first predetermined period has not elapsed, the method 2500 continues to provide a microwave signal to the antenna in step 2502.

If the first predetermined period has elapsed, the microwave signal is turned off in step 2506 and a first noise temperature is measured by the radiometer in step 2508. The first noise temperature may be measured immediately after the microwave signal is turned off. In step 2510, the noise temperature is measured and the slope of a noise temperature curve is calculated. The slope of the noise temperature curve may be calculated based on the current noise temperature and one or more previous noise temperature measurements. In step 2512, it is determined whether the calculated slope is approximately equal to a predetermined slope which indicates that the temperature of the transmission network has reached a reference temperature and that the measured noise temperature represents the noise temperature of the tissue. If it is determined that the calculated slope is not approximately equal to the predetermined slope, then the method 2500 returns to step 2510 to measure the noise temperature and calculate the slope to the noise temperature curve.

If it is determined in step 2512 that the calculated slope is approximately equal to the predetermined slope, a second noise temperature is measured by the radiometer and is recorded as the noise temperature of the tissue, in step 2514. In step 2516, the difference between the first noise temperature and the second noise temperature is determined and recorded as the noise temperature of the transmission network. Then, in step 2518, the method 2500 waits until the second predetermined period elapses before returning to step 2502 to turn on the microwave signal.

The above-described microwave ablation systems are capable of directing microwave energy into tissue, and may be suitable for use in a variety of procedures and operations. The above-described microwave ablation systems may be suitable for utilization with hand-assisted, endoscopic and laparoscopic surgical procedures. The above-described microwave ablation systems may also be suitable for utilization in open surgical applications.

An aspect of the present disclosure is the use of the microwave ablation systems described above used for treatment of cancers and other diseases of the lungs. Location and treatment of lung diseases, particularly cancers due to smoking, is quite challenging due to the tortuous paths of the lung passages, the extremely small size of peripheral lung passages, and the movement of the lungs during both diagnostic procedures and treatments.

An effective method of identifying cancerous or diseased target tissue involves the use of a computed tomographic (CT) image. The use of CT as a diagnostic tool has now become routine and CT results are now frequently the primary source of information available to the practitioner regarding the size and location of a lesion. This information is used by the practitioner in planning an operative procedure such as a biopsy, but is only available as "offline" information which must typically be memorized to the best of the practitioner's ability prior to beginning a procedure. As described below, in addition to inputting target information, integration with the CT data provides improved system functionality, thereby greatly facilitating the planning of a pathway to an identified target as well as providing the ability to navigate through the body to the target location.

The microwave ablation systems according to the present disclosure may employ systems and methods for constructing, selecting and presenting pathway(s) to a target location within an anatomical luminal network in a patient. These systems and methods are particularly, but not exclusively, suited for guiding and navigating a probe, e.g., the microwave applicator 800 of FIG. 8, through the bronchial airways of the lungs. These systems and methods include a preoperative and a operative component. The preoperative component is conducted prior to navigation and can be categorized as pathway planning. The operative component is conducted during navigation and can be categorized as navigation.

The pathway planning phase includes three general steps, which are described in more detail in commonly assigned U.S. application Ser. No. 13/834,581 entitled "MICROWAVE ENERGY-DELIVERY DEVICE AND SYSTEM," and U.S. application Ser. No. 13/838,805 entitled "PATHWAY PLANNING SYSTEM AND METHOD," the entire contents of each of which are incorporated herein by reference. The first step involves using a software graphical interface for generating and viewing a three-dimensional model of the bronchial airway tree ("BT"). The second step involves using the software graphical interface for selection of a pathway on the BT, either automatically, semi-automatically, or manually, if desired. The third step involves an automatic segmentation of the pathway(s) into a set of waypoints along the path that can be visualized on a display. It is to be understood that the airways are being used herein as an example of a branched luminal anatomical network. Hence, the term "BT" is being used in a general sense to represent any such luminal network and not to be construed to only refer to a bronchial tree, despite that the initials "BT" may not apply to other networks.

Having identified a pathway in the BT connecting the trachea in a CT image with a target, a system is necessary to reach the target with the microwave applicator 800 in the navigation phase. One such system is described in commonly assigned U.S. application Ser. No. 13/834,581 entitled "MICROWAVE ENERGY-DELIVERY DEVICE AND SYSTEM."

CT data (images) may be employed for the route planning phase. CT data is also used for the navigation phase. CT data is preferable to other imaging modalities because it has its own system of coordinates. Matching the two systems of coordinates, that of the CT and that of the patient, is commonly known as registration. Registration is generally performed by identifying locations in both the CT and on or inside the body, and measuring their coordinates in both systems.

Methods of manual and semi-automated registration of CT data and patient data are described in detail in for example U.S. Pat. No. 7,233,820 assigned to Covidien LP and incorporated herein by reference. While still a viable methods of registration, because particularly manual registration is somewhat time consuming and requires multiple steps, many practitioners rely on the automatic registration techniques the software of the current disclosure enables. However, in some instances, particularly if the CT image data is not of sufficient quality it may still be necessary or desirable to conduct manual registration.

Automatic registration has become the norm for most procedures because while the manual fiducial point designation of the above referenced registration techniques is highly effective, the choice of number of points sampled necessarily represents a tradeoff between accuracy and efficiency. Similarly, while the semi-automated technique is a viable option it requires an image sensor at the distal end of the catheter assembly which adds increased complexity to the system.

Automatic registration techniques are described in detail in commonly assigned U.S. patent application Ser. No. 12/780, 678, which is incorporated herein by reference. Automatic registration between a digital image of a branched structure and a real-time indicator representing a location of a sensor inside the branched structure is achieved by using a sensor to "paint" a digital picture of the inside of the structure. Once enough location data has been collected, registration is achieved. The registration is "automatic" in the sense that navigation through the branched structure necessarily results in the collection of additional location data and, as a result, registration is continually refined.

Once the targets have been identified, the pathway planned, the bronchoscope including locatable guide inserted into the patient, and the virtual bronchoscopy image registered with the image data of the bronchoscope, the system is ready to navigate a location sensor to the target within the patient's lungs. A computer provides a display identifying the target and depicting the virtual bronchoscopy image. However, appearing in each of the images on the display is the pathway from the current location of the location sensor to the target. This is the pathway that was established during the pathway planning phase discussed above. The pathway may be represented, for example, by a colored line. Also appearing in each image is a representation of the distal tip of the locatable guide and location sensor. By advancing the locatable guide and following the pathway the medical professional is able to follow the identified pathway to the target. At times, as discussed above, the virtual bronchoscopy image may not provide sufficient accuracy, particularly at the pleura boundaries of the lungs. In such instances the user can rely on the CT images to provide greater details.

Although the position of the location sensor is measured in real time, the target location is not. The target is generally considered fixed relative to the patient's body position which is monitored in real time by sensors. However, navigation accuracy may decrease as a result of cyclic chest movement resulting from breathing. Preferably, precautions are taken to reduce the effects of this cyclic movement including reducing the respiration rate of the patient. In addition this movement may be accounted for in the software by sampling the position sensors positions selectively so that measurements are only made at an extreme of a cyclic motion. The extremes of the motion of the patient's chest can readily be identified by the cyclic displacement of sensors during the breathing cycle. It may be preferred to use the maximum exhalation state for measurements since this state typically remains steady for a relatively larger proportion of the breath cycle than the maximum inhalation state. Alternatively, measurements can be taken continuously, and the cyclic variations eliminated or reduced by additional processing. This processing may include applying a low-frequency filter to the measurements. Alternatively, an average of the measurements over a time period of the cyclic motion may be calculated and used to assist in approximating the location of the target. This is assisted by knowing whether the CT data was derived with the patient in a fully inhaled or exhaled position, which can be used for comparison and greater approximation of positioning.

Once the locatable guide has successfully been navigated to the target location, the locatable guide is preferably removed, leaving a sheath in place as a guide channel for bringing a tool, e.g., the microwave applicator 800, to the target location.

The planning and navigation systems and methods of the present disclosure may employ markers. These markers can be used for a variety of purposes including identifying tumors and lesions for follow-up analysis and monitoring, to identify locations that biopsy sampling has been undertaken, and to identify the boundaries or the center of a tumor or lesion for application of treatment. Other uses will be understood by those of skill in the art as falling within the scope of the present disclosure. The placement of markers can be particularly useful in the context of performing a video assisted thoracoscopic surgery (VATS) lung procedure, which is described in more detail in commonly assigned U.S. application Ser. No. 13/834,581, the disclosure of which is incorporated herein by reference.

A variety of techniques for identification of the location of implanted markers can be employed including fluoroscopy, ultrasound, and other imaging modalities. These are particularly useful when the marker is equipped with a radio-opaque portion, formed of, for example, gold. VATS procedures in particular lend themselves to visual identification, particularly when performing treatment of tissues near the pleura boundaries of the lungs. Some techniques to improve visualization involve the injection of inks or dyes into the patient to identify the location of the marker. These techniques tend to be more of a clinician based ad hoc solution to visual identification.

As an initial matter visualizing of markers of any kind, especially in a discolored and diseased lung tissue, can be very difficult. Further, traditional dyes and solutions tend to be spread too broadly for accurate identification of the tissue to be identified, particularly if the marker is placed more than a few hours before the surgical procedure. Typically surgery must be undertaken within 72 hours of dye injection. Gold fiducial markers on the other hand are difficult if not impossible to identify without some imaging modality, and sometimes currently available fiducial markers tend to migrate over time, or even as a result of a patient cough.

As described in commonly assigned U.S. application Ser. No. 13/834,581, the disclosure of which is incorporated herein by reference, one embodiment of the planning and navigation systems and methods is directed to placement of a marker to promote visual identification of the tissue of interest during VATS and so that the tissue can be percutaneously ablated using the microwave ablation systems described above.

Though described herein with respect to a particular planning and navigation system, other pathway planning and navigation systems may be employed without departing from the scope of the present disclosure. For example, the systems described in commonly assigned U.S. patent application Ser. Nos. 13/477,279; 13/477,291; 13/477,374; 13/477,395; 13/477,406; and 13/477,417, the entire contents of each of which are incorporated herein by reference, as well as those systems described for example is U.S. Pat. No. 7,876,942 currently assigned to Activiewes, LTD.

Though described here with respect to treatment of lung tissue, embodiments of the present disclosure are equally applicable for use in treatment of other tissues. For example, it is contemplated that the systems and methods of the present disclosure may be used to treat liver tissue, kidney tissue, pancreatic tissue, gastrointestinal tissue, interstitial masses, and other portions of the body known to those of skill in the art to be treatable via microwave ablation.

The microwave applicators, which may be embodied as handpieces, cables, and thermometry modules (generally referred to as devices) described in the present disclosure may include one or more data storage components (e.g., EEPROM, PROM, etc.) capable of storing data therein for identifying the device. The stored data may include identification data of the device as well as data related to usage of the device (e.g., number of activations or time stamps of usage) and data related to reprocessing of the device. The data read from the data storage component may be read by other components of the system, such as the microwave generator 1000 of FIG. 10, to ensure that the device is compatible with the other components of the system, is permitted to operate in a particular geographic location, has not exceeded a defined usage count or usage time, and is reasonably assured of being sterile.

The device may alternatively include a bar code identifying the device and a microwave generator or other component of the microwave ablation system may include a bar code reader for reading identification data from the bar code. The bar code reader may then provide the read identification data to a computer connected to the bar code reader so that the computer can track the use of the device.

One method of preventing unintended usage of a device is to limit the number of usages before requiring reprocessing of the device. As an example related to a single use device, following connection of a device (e.g., the microwave applicator 800 of FIG. 8) to a generator (e.g., microwave generator 1000 of FIG. 10), or following the device's initial use, a time stamp may be written to a data field of a data storage component. This data field may be continually checked to ensure that too great a period of time has not elapsed since that time stamp. Either simultaneously with the connection/activation of the device or following the expiry of the permitted usage time from the initial time stamp, data may be written to a separate data field in the data storage component. In the example of a single use device, once the data field has any data written to it that can be read by the other components of the system, the other components will refuse to permit the device's use and may provide a message to the user that the device must be sent for reprocessing. Other usage schemes may also be used as would be appreciated by one of ordinary skill in the art without departing from the scope of the present disclosure.

Reprocessing may be performed in an authorized reprocessing facility where the device may be inspected, worn parts may be replaced, data stored on the data storage components may be read, and the device may be sterilized. The data read from the data storage component may be sent back to the original manufacturer for review and analysis. The data storage component may include a data field identifying the number of times the device has been reprocessed. This data field is updated each time the device is reprocessed.

The number of times a device may be reprocessed may be limited as well. Accordingly upon reaching the specified limit the device must be completely destroyed. As part of the reprocessing, the time stamp described above from insertion into another component or first activation may be overwritten and thus the device upon next insertion into another component is usable. While described generally herein, with respect to a limited example, reprocessing may under take a variety of schemes and a number of data fields on the data storage component may be read, overwritten, or have data written to them to ensure the safety and sterility of the devices.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation system comprising:
a microwave applicator including an antenna configured to deliver microwave energy to ablate tissue;
a microwave generator coupled to the microwave applicator and configured to generate a microwave signal and transmit the microwave signal to the antenna via a transmission network;
a thermometry circuit coupled between the microwave generator and the microwave applicator, the thermometry circuit including a radiometer configured to measure a noise temperature signal and a coupling network coupled to the transmission network and configured to provide a noise temperature signal propagating in the transmission network to the radiometer; and
a controller coupled to the thermometry circuit and configured to calculate a temperature value based on the noise temperature signal,
wherein the thermometry circuit further includes:
a first filter configured to isolate the noise temperature signal from the microwave signal and output the noise temperature signal; and
a second filter configured to filter the noise temperature signal output from the first filter.

2. The microwave ablation system according to claim 1, wherein the transmission network includes a microwave cable connected between the microwave applicator and the microwave generator,
wherein the thermometry circuit is integrated into the microwave applicator, the microwave generator, or the microwave cable.

3. The microwave ablation system according to claim 1, wherein the second filter is further configured to obtain a noise temperature signal from the tissue and a noise temperature signal from a component of the microwave ablation system.

4. The microwave ablation system according to claim 3, wherein the component of the microwave ablation system is a microwave cable connected between the microwave applicator and the microwave generator.

5. The microwave ablation system according to claim 3, wherein the second filter is further configured to determine the noise temperature of the component of the microwave ablation system by analyzing the noise temperature signal at different frequencies.

6. The microwave ablation system according to claim 1, wherein the coupling network couples a portion of the signals propagating through the transmission network to the radiometer.

7. The microwave ablation system according to claim 6, wherein the coupling network is a directional coaxial coupler.

8. The microwave ablation system according to claim 1, wherein the coupling network is a switch configured to switch from a connection between the antenna and the microwave generator to a connection between the antenna and the radiometer.

9. The microwave ablation system according to claim 1, wherein the coupling network is a T-network having a first band pass filter for passing the noise temperature signal to the radiometer and a second band pass filter for passing the microwave signal to the antenna.

10. The microwave ablation system according to claim 1, wherein the radiometer comprises:
   a low-noise amplifier configured to amplify the temperature noise signal;
   a detector coupled to the output of the low-noise amplifier and configured to detect the noise temperature signal; and
   an integrator coupled to the output of the detector.

11. The microwave ablation system according to claim 10, wherein the radiometer further comprises:
   a local oscillator;
   a mixer coupled to the output of the low-noise amplifier and the output of the local oscillator, the mixer being configured to mix the amplified noise temperature signal with the output from the local oscillator;
   an intermediate frequency band pass filter coupled to the output of the mixer, the intermediate frequency band pass filter having a predetermined bandwidth; and
   an intermediate frequency amplifier coupled to the output of the intermediate frequency band pass filter.

12. The microwave ablation system according to claim 11, wherein the predetermined bandwidth is within ±35 MHz.

13. The microwave ablation system according to claim 10, wherein the radiometer further comprises:
   a resistive load maintained at a constant temperature; and
   a switch coupled to the input of the low-noise amplifier and configured to switch the input to the low-noise amplifier between the antenna and the resistive load.

14. The microwave ablation system according to claim 13, wherein the resistive load is a thermocouple disposed in thermal communication with the transmission network.

15. The microwave ablation system according to claim 10, wherein the integrator is configured to integrate over a long period from 10 milliseconds to 10 seconds.

16. The microwave ablation system according to claim 10, wherein the controller is further configured to calibrate the radiometer to the temperature of a body whose tissue is being treated by the microwave applicator.

17. The microwave ablation system according to claim 1, wherein the controller is further configured to control the microwave generator based on the temperature value.

18. A microwave ablation device comprising:
   an antenna configured to deliver microwave energy to ablate tissue; and
   a handle assembly attached to the antenna, the handle assembly including a thermometry circuit coupled to the antenna via a transmission network, the thermometry circuit including:
   a radiometer configured to measure a noise temperature signal;
   a coupling network coupled to the transmission network and configured to provide a noise temperature signal propagating in the transmission network to the radiometer; and
   a controller coupled to the thermometry circuit and configured to calculate a temperature value based on the noise temperature signal,
   wherein the thermometry circuit further includes:
   a first filter configured to isolate the noise temperature signal from a microwave signal propagating in the transmission network and output the noise temperature signal; and
   a second filter configured to filter the noise temperature signal output from the first filter.

19. The microwave ablation device according to claim 18, wherein second filter is further configured to filter the output from the first filter to obtain a noise temperature signal from the tissue and a noise temperature signal from the transmission network.

20. The microwave ablation device according to claim 18, wherein the second filter is further configured to determine the noise temperature of a component of the microwave ablation device by analyzing the noise temperature signal at different frequencies.

* * * * *